United States Patent
Sharma et al.

(10) Patent No.: US 11,851,707 B1
(45) Date of Patent: Dec. 26, 2023

(54) N-MYC-INTERACTOR PROTEIN AS A MARKER FOR CHRONIC LUNG DISEASE AND USES THEREOF

(71) Applicant: University of South Florida, Tampa, FL (US)

(72) Inventors: Nirmal S. Sharma, Tampa, FL (US); Mudassir Banday, Tampa, FL (US); Andreas Seyfang, Tampa, FL (US)

(73) Assignee: University of South Florida, Tampa, FL (US)

( * ) Notice: Subject to any disclaimer, the term of this patent is extended or adjusted under 35 U.S.C. 154(b) by 303 days.

(21) Appl. No.: 17/215,249

(22) Filed: Mar. 29, 2021

Related U.S. Application Data

(60) Provisional application No. 63/000,999, filed on Mar. 27, 2020.

(51) Int. Cl.
*C12Q 1/6883* (2018.01)
*A61K 9/00* (2006.01)
*A61K 9/51* (2006.01)

(52) U.S. Cl.
CPC .......... *C12Q 1/6883* (2013.01); *A61K 9/0043* (2013.01); *A61K 9/51* (2013.01); *C12Q 2600/118* (2013.01); *C12Q 2600/158* (2013.01)

(58) Field of Classification Search
CPC ............ C12Q 1/6883; C12Q 2600/118; C12Q 2600/158; A61K 9/0043; A61K 9/51
See application file for complete search history.

(56) References Cited

U.S. PATENT DOCUMENTS 5,460,831 A * 10/1995 Kossovsky ............ A61K 48/00
424/490

OTHER PUBLICATIONS

Weigt et al (Gene expression profiling of bronchoalveolar lavage cells preceding a clinical diagnosis of chronic lung allograft dysfunction), Research Article, PLOS One, pp. 1-17 (Year: 2017).*
Vos R. et al. Pseudomonal airway colonisation: risk factor for bronchiolitis obliterans syndrome after lung transplantation? Eur Respir J. 2008;31(5):1037-1045.
Gottlieb J. et al. Impact of graft colonization with gram negative bacteria after lung transplantation on the development of bronchiolitis obliterans syndrome in recipients with cystic fibrosis. Respiratory medicine. 2009;103(5):743-749.
Charlson E.S. et al. Lung-enriched organisms and aberrant bacterial and fungal respiratory microbiota after lung transplant. American journal of respiratory and critical care medicine. 2012; 186(6):536-545.
Bernasconi E. et al. Airway Microbiota Determines Innate Cell Inflammatory or Tissue Remodeling Profiles in Lung Transplantation. American journal of respiratory and critical care medicine. 2016;194(10): 1252-1263.

Sharma N.S. et al. Distal airway microbiome is associated with immunoregulatory myeloid cell responses in lung transplant recipients. The Journal of heart and lung transplantation : the official publication of the International Society for Heart Transplantation. 2017;37(2):P206.
Sharma N.S. et al. Differences in airway microbiome and metabolome of single lung transplant recipients. Respir Res. 2020;21(1):104.
Dickson R.P. et al. Changes in the lung microbiome following lung transplantation include the emergence of two distinct Pseudomonas species with distinct clinical associations. PLOS One. 2014;9(5):e97214.
Metwally A.A. et al. Pediatric lung transplantation: Dynamics of the microbiome and bronchiolitis obliterans in cystic fibrosis. The Journal of heart and lung transplantation : the official publication of the International Society for Heart Transplantation. 2020;39(8):824-834.
Wu Q. et al. Gut Microbiota Can Impact Chronic Murine Lung Allograft Rejection. Am J Respir Cell Mol Biol. 2019;60 (1):131-134.
Schott C. et al. Bronchiolitis obliterans syndrome susceptibility and the pulmonary microbiome. The Journal of heart and lung transplantation : the official publication of the International Society for Heart Transplantation. 2018;37 (9):1131-1140.
Willner D.L. et al. Reestablishment of recipient-associated microbiota in the lung allograft is linked to reduced risk of bronchiolitis obliterans syndrome. American journal of respiratory and critical care medicine. 2013;187(6):640-647.
O'Dwyer D.N. et al. Lung Microbiota Contribute to Pulmonary Inflammation and Disease Progression in Pulmonary Fibrosis. American journal of respiratory and critical care medicine. 2019;199(9):1127-1138.
O'Dwyer D.N. et al. Lung Dysbiosis, Inflammation, and Injury in Hematopoietic Cell Transplantation. Am J Respir Crit Care Med. 2018.
Hentschke I. et al. IL-33/ST2 immune responses to respiratory bacteria in pediatric asthma. Sci Rep. 2017;7:43426.

(Continued)

*Primary Examiner* — Mina Haghighatian
(74) *Attorney, Agent, or Firm* — Michele L. Lawson; Smith & Hopen, P.A.

(57) ABSTRACT

A method of predicting the development of chronic lung allograft dysfunction (CLAD) in lung transplant patients using N-myc-interactor (NMI) as a biomarker and associated treatment thereof is presented. Also presented is a method of reducing the risk of CLAD by administering a therapeutic agent capable of increasing NMI in the patient. NMI is a critical regulator of epithelial-to-mesenchymal transition (EMT) and an important precursor to development of CLAD. NMI expression is reduced in CLAD patients and can be used as an early diagnostic biomarker to predict the development of CLAD. NMI can also be used as a drug target for a therapeutic to increase expression of NMI and treat chronic lung disease such as CLAD. Therapeutics comprising NMI protein or NMI gene can be used as potential treatments for chronic lung diseases such as CLAD.

4 Claims, 15 Drawing Sheets

Specification includes a Sequence Listing.

(56) References Cited

OTHER PUBLICATIONS

Borthwick L.A. et al. Epithelial to mesenchymal transition (EMT) and airway remodelling after human lung transplantation. Thorax. 2009;64(9):770-777.

Salton F. et al. Epithelial-Mesenchymal Transition in the Pathogenesis of Idiopathic Pulmonary Fibrosis. Medicina (Kaunas). 2019;55(4):83.

Rout-Pitt N. et al. Epithelial mesenchymal transition (EMT): a universal process in lung diseases with implications for cystic fibrosis pathophysiology. Respir Res. 2018;19(1):136.

Devine D.J. et al. Loss of N-Myc interactor promotes epithelial-mesenchymal transition by activation of TGF-beta/SMAD signaling. Oncogene. 2014;33(20):2620-2628.

Fillmore R.A. et al. Nmi (N-Myc interactor) inhibits Wnt/beta-catenin signaling and retards tumor growth. Int J Cancer. 2009; 125(3):556-564; Feng X, Xu X, Xiao X, et al. NMI inhibits cancer stem cell traits by downregulating hTERT in breast cancer. Cell Death Dis. 2017;8(5):e2783.

Feng L. et al. Human cytomegalovirus UL23 inhibits transcription of interferon-gamma stimulated genes and blocks antiviral interferon-gamma responses by interacting with human N-myc interactor protein. PLOS Pathog. 2018; 14(1): e1006867.

Hou J. et al. N-Myc-interacting protein (NMI) negatively regulates epithelial-mesenchymal transition by inhibiting the acetylation of NF-kappaB/p65. Cancer Lett. 2016;376(1):22-33.

Hou J. et al. N-Myc-Interacting Protein Negatively Regulates TNFalpha-Induced NF-kappaB Transcriptional Activity by Sequestering NF-kappaB/p65 in the Cytoplasm. Sci Rep. 2017;7(1):14579.

Botha P. et al. Pseudomonas aeruginosa colonization of the allograft after lung transplantation and the risk of bronchiolitis obliterans syndrome. Transplantation. 2008;85(5):771-774.

Nakajima T. et al. Lung transplantation: infection, inflammation, and the microbiome. Semin Immunopathol. 2011;33 (2):135-156.

Belperio J.A. et al. Bronchiolitis obliterans syndrome complicating lung or heart-lung transplantation. Seminars in respiratory and critical care medicine. 2003;24(5):499-530.

Belperio J.A. et al. Chronic lung allograft rejection: mechanisms and therapy. Proceedings of the American Thoracic Society. 2009;6(1):108-121.

Renaud-Picard B. et al. Epithelial-mesenchymal transition and membrane microparticles: Potential implications for bronchiolitis obliterans syndrome after lung transplantation. Transpl Immunol. 2020;59:101273.

Bartis D. et al. Epithelial-mesenchymal transition in lung development and disease: does it exist and is it important? Thorax. 2014;69(8):760-765.

Wang J. et al. Downregulation of NMI promotes tumor growth and predicts poor prognosis in human lung adenocarcinomas. Mol Cancer. 2017; 16(1):158.

Tissot, A. et al. Early Identification of Chronic Lung Allograft Dysfunction: The Need of Biomarkers. Front. Immuno. 10, 1618-1631 (2019).

Whitfield, J.R. et al. Tumor microenvironment: becoming sick of Myc. Cell. Mol. Life Sci. 69, 931-934 (2012).

Verleden, S.E. et al. Chronic Lung Allograft Dysfunction Phenotypes and Treatment. J. Thorac. Dis. 9(8) 2650-2659 (2017).

* cited by examiner

SEQUENCE LISTING

```
<160> NUMBER OF SEQ ID NOS: 4

<210> SEQ ID NO 1
<211> LENGTH: 60
<212> TYPE: DNA
<213> ORGANISM: Homo sapiens
<220> FEATURE:
<221> NAME/KEY: misc_feature
<222> LOCATION: (50)..(50)
<223> OTHER INFORMATION: M is A or C

<400> SEQUENCE: 1
aatgatacgg cgaccaccga gatctacact atggtaattg tgtgccagcm gccgcggtaa    60

<210> SEQ ID NO 2
<211> LENGTH: 61
<212> TYPE: DNA
<213> ORGANISM: Homo sapiens
<220> FEATURE:
<221> NAME/KEY: misc_feature
<222> LOCATION: (24)..(29)
<223> OTHER INFORMATION: n is A, C, G or T
<220> FEATURE:
<221> NAME/KEY: misc_feature
<222> LOCATION: (50)..(50)
<223> OTHER INFORMATION: v is A, C, or G
<220> FEATURE:
<221> NAME/KEY: misc_feature
<222> LOCATION: (55)..(55)
<223> OTHER INFORMATION: w is A or T

<400> SEQUENCE: 2
caagagaaga cggcatacga gatnnnnnna gtcagtcagc cggactachv gggtwtctaa    60
t                                                                    61
```

```
<210> SEQ ID NO 3
<211> LENGTH: 22
<212> TYPE: DNA
<213> ORGANISM: Homo sapiens

<400> SEQUENCE: 3
gcaggcctaa cacatgcaag tc                                              22

<210> SEQ ID NO 4
<211> LENGTH: 20
<212> TYPE: DNA
<213> ORGANISM: Homo sapiens

<400> SEQUENCE: 4
ctgctgcctc ccgtaggagt                                                 20
```

N-MYC-INTERACTOR PROTEIN AS A MARKER FOR CHRONIC LUNG DISEASE AND USES THEREOF

CROSS REFERENCE TO RELATED APPLICATIONS

This application is a nonprovisional of and claims priority to U.S. Provisional Application No. 63/000,999 entitled "N-Myc-Interactor Protein as a Marker for Chronic Lung Disease and Uses Thereof", filed Mar. 27, 2020, the contents of which are hereby incorporated by reference into this disclosure.

FIELD OF INVENTION

This invention relates to biomarkers. Specifically, the invention provides the use of N-Myc-Interactor (NMI) protein as a biomarker for diagnosis and/or as a pharmaceutical agent, recombinant protein or gene therapy treatment for chronic lung disease.

BACKGROUND OF THE INVENTION

Long-term survival of lung transplant recipients is limited by chronic lung allograft dysfunction (CLAD), commonly termed chronic rejection. (Burton C M, Carlsen J, Mortensen J, Andersen C B, Milman N, Iversen M. Long-term survival after lung transplantation depends on development and severity of bronchiolitis obliterans syndrome. *The Journal of heart and lung transplantation: the official publication of the International Society for Heart Transplantation.* 2007; 26(7):681-686; Annual Data Report of the US Organ Procurement and Transplantation Network. Preface. *American journal of transplantation: official journal of the American Society of Transplantation and the American Society of Transplant Surgeons.* 2014; 14 Suppl 1:5-7). At 5-years post transplantation fifty percent of recipients are diagnosed with CLAD; furthermore the median survival after onset of CLAD is a mere 3 years. (Estenne M, Hertz M I. Bronchiolitis obliterans after human lung transplantation. *American journal of respiratory and critical care medicine.* 2002; 166(4):440-444; Belperio J A, Lake K, Tazelaar H, Keane M P, Strieter R M, Lynch J P, 3rd. Bronchiolitis obliterans syndrome complicating lung or heart-lung transplantation. *Seminars in respiratory and critical care medicine.* 2003; 24(5):499-530).

Recent studies have identified a potential role for lung microbiome in pathogenesis and/or progression of chronic lung diseases. (Vos R, Vanaudenaerde B M, Geudens N, Dupont L J, Van Raemdonck D E, Verleden G M. Pseudomonal airway colonisation: risk factor for bronchiolitis obliterans syndrome after lung transplantation? *Eur Respir J.* 2008; 31(5):1037-1045; Gottlieb J, Mattner F, Weissbrodt H, et al. Impact of graft colonization with gram negative bacteria after lung transplantation on the development of bronchiolitis obliterans syndrome in recipients with cystic fibrosis. *Respiratory medicine.* 2009; 103(5):743-749; Charlson E S, Diamond J M, Bittinger K, et al. Lung-enriched organisms and aberrant bacterial and fungal respiratory microbiota after lung transplant. *American journal of respiratory and critical care medicine.* 2012; 186(6):536-545; Bernasconi E, Pattaroni C, Koutsokera A, et al. Airway Microbiota Determines Innate Cell Inflammatory or Tissue Remodeling Profiles in Lung Transplantation. *American journal of respiratory and critical care medicine.* 2016; 194(10):1252-1263; Sharma N S, Wille K M, Athira S, et al. Distal airway microbiome is associated with immunoregulatory myeloid cell responses in lung transplant recipients. *The Journal of heart and lung transplantation: the official publication of the International Society for Heart Transplantation.* 2017; 37(2):P206; Sharma N S, Vestal G, Wille K, et al. Differences in airway microbiome and metabolome of single lung transplant recipients. *Respir Res.* 2020; 21(1): 104).

The inventors and others have shown that lung microbial dysbiosis is associated with CLAD. (Bernasconi E, Pattaroni C, Koutsokera A, et al. Airway Microbiota Determines Innate Cell Inflammatory or Tissue Remodeling Profiles in Lung Transplantation. *American journal of respiratory and critical care medicine.* 2016; 194(10):1252-1263; Sharma N S, Wille K M, Athira S, et al. Distal airway microbiome is associated with immunoregulatory myeloid cell responses in lung transplant recipients. *The Journal of heart and lung transplantation: the official publication of the International Society for Heart Transplantation.* 2017; 37(2):P206; Dickson R P, Erb-Downward J R, Freeman C M, et al. Changes in the lung microbiome following lung transplantation include the emergence of two distinct *Pseudomonas* species with distinct clinical associations. *PLoS One.* 2014; 9(5): e97214; Metwally A A, Ascoli C, Turturice B, et al. Pediatric lung transplantation: Dynamics of the microbiome and bronchiolitis obliterans in cystic fibrosis. *The Journal of heart and lung transplantation: the official publication of the International Society for Heart Transplantation.* 2020; 39(8):824-834).

The inventors previously reported that a shift from a Firmicute dominant to a Proteobacteria dominant microbiome is associated with CLAD. (Sharma N S, Wille K M, Athira S, et al. Distal airway microbiome is associated with immunoregulatory myeloid cell responses in lung transplant recipients. *The Journal of heart and lung transplantation: the official publication of the International Society for Heart Transplantation.* 2017; 37(2):P206). Furthermore, some of the associations between microbial dysbiosis and CLAD have been validated using animal transplantation models. (Wu Q, Turturice B, Wagner S, et al. Gut Microbiota Can Impact Chronic Murine Lung Allograft Rejection. *Am J Respir Cell Mol Biol.* 2019; 60(1):131-134). More recently, a report suggested that presence of certain gram-positive bacteria enriched pulmonary microbiome from phylum Actinobacteria may be protective against CLAD. (Schott C, Weigt S S, Turturice B A, et al. Bronchiolitis obliterans syndrome susceptibility and the pulmonary microbiome. *The Journal of heart and lung transplantation: the official publication of the International Society for Heart Transplantation.* 2018; 37(9):1131-1140). Likewise, infection with new bacterial species that are divergent from the pre-lung transplant microbiome in cystic fibrosis patients who underwent lung transplantation, have been implicated in the occurrence of CLAD, while retention of the pre-transplant microbiome may be protective from CLAD. (Willner D L, Hugenholtz P, Yerkovich S T, et al. Reestablishment of recipient-associated microbiota in the lung allograft is linked to reduced risk of bronchiolitis obliterans syndrome. *American journal of respiratory and critical care medicine.* 2013; 187(6):640-647).

Delineation of the lung microbiome signatures in various disease states is an important first step but does not directly provide an insight into host-microbiome interaction. Several studies have evaluated the impact of dysbiotic lung microbiome on the host immune response. (O'Dwyer D N, Ashley S L, Gurczynski S J, et al. Lung Microbiota Contribute to Pulmonary Inflammation and Disease Progression in Pulmonary Fibrosis. *American journal of respiratory and critical care medicine.* 2019; 199(9):1127-1138.; O'Dwyer D N, Zhou X, Wilke C A, et al. Lung Dysbiosis, Inflammation, and Injury in Hematopoietic Cell Transplantation. *Am J Respir Crit Care Med.* 2018; Hentschke I, Graser A, Melichar V O, et al. IL-33/ST2 immune responses to respiratory bacteria in pediatric asthma. *Sci Rep.* 2017; 7:43426). The inventors have previously shown that the lung microbiome is associated with the recruitment of specific phenotypic subsets of airway myeloid derived suppressor cells and activation of matrikine peptides. (Sharma N S, Wille K M, Athira S, et al. Distal airway microbiome is associated with immunoregulatory myeloid cell responses in lung transplant recipients. *The Journal of heart and lung transplantation: the official publication of the International Society for Heart Transplantation.* 2017; 37(2):P206; Sharma N S, Vestal G, Wille K, et al. Differences in airway microbiome and metabolome of single lung transplant recipients. *Respir Res.* 2020; 21(1):104). Likewise, pro-inflammatory bacteria such as *Staphylococcus* and *Pseudomonas* are known to trigger genes encoding for catabolic remodeling, while commensals such as *Prevotella* and *Veilonella* correlate with activation of genes encoding for anabolic remodeling in the lung. (Bernasconi E, Pattaroni C, Koutsokera A, et al. Airway Microbiota Determines Innate Cell Inflammatory or Tissue Remodeling Profiles in Lung Transplantation. *American journal of respiratory and critical care medicine.* 2016; 194(10):1252-1263). While several associations of host-microbiome interactions have been reported, the precise mechanisms behind the microbiome-allograft interactions leading to chronic lung inflammation and CLAD have not yet been delineated.

Epithelial-to-mesenchymal transition is an evolutionary process that has a key role in repair and regeneration of the lung tissue. (Bartis D, Mise N, Mahida R Y, Eickelberg O, Thickett D R. Epithelial-mesenchymal transition in lung development and disease: does it exist and is it important? *Thorax.* 2014; 69(8):760-765). However, dysregulated EMT is a key pathological feature identified in the occurrence of chronic lung diseases such as idiopathic pulmonary fibrosis (IPF) and CLAD. (Borthwick L A, Parker S M, Brougham K A, et al. Epithelial to mesenchymal transition (EMT) and airway remodelling after human lung transplantation. *Thorax.* 2009; 64(9):770-777; Salton F, Volpe M C, Confalonieri M. Epithelial(-)Mesenchymal Transition in the Pathogenesis of Idiopathic Pulmonary Fibrosis. *Medicina (Kaunas).* 2019; 55(4):83).

Pathologic EMT leading to disease can be triggered by several processes including hypoxia, toxins and infections that trigger breakdown of extracellular membrane and release of TGF-β leading to activation of downstream signaling. (Rout-Pitt N, Farrow N, Parsons D, Donnelley M. Epithelial mesenchymal transition (EMT): a universal process in lung diseases with implications for cystic fibrosis pathophysiology. *Respir Res.* 2018; 19(1):136). These processes result in transformation of a polarized epithelial cell to a mesenchymal phenotype characterized by the loss in expression of epithelial markers such as E-cadherin and keratin, and gain in mesenchymal markers such as vimentin, N-cadherin and smooth muscle actin. (Bartis D, Mise N, Mahida R Y, Eickelberg O, Thickett D R. Epithelial-mesenchymal transition in lung development and disease: does it exist and is it important? *Thorax.* 2014; 69(8):760-765; Rout-Pitt N, Farrow N, Parsons D, Donnelley M. Epithelial mesenchymal transition (EMT): a universal process in lung diseases with implications for cystic fibrosis pathophysiology. *Respir Res.* 2018; 19(1):136).

N-myc-interactor (NMI) protein, also known as N-myc and STAT interactor, is a signaling transduction protein and a key transcriptional regulator of genes including genes that modulate EMT. (Devine D J, Rostas J W, Metge B J, et al. Loss of N-Myc interactor promotes epithelial-mesenchymal transition by activation of TGF-beta/SMAD signaling. *Oncogene.* 2014; 33(20):2620-2628). Previous studies have shown that downregulation of NMI predicts tumor invasion and metastasis in several cancers via upregulation of the TGF-β/SMAD signaling pathway. (Fillmore R A, Mitra A, Xi Y, et al. Nmi (N-Myc interactor) inhibits Wnt/beta-catenin signaling and retards tumor growth. *Int J Cancer.* 2009; 125(3):556-564; Feng X, Xu X, Xiao X, et al. NMI inhibits cancer stem cell traits by downregulating hTERT in breast cancer. *Cell Death Dis.* 2017; 8(5):e2783).

Conversely, cytokines such as IFN-7 can activate NMI and inhibit the acetylation of p65 via the NF-κB pathway and modulate antiviral host response. (Feng L, Sheng J, Vu G P, et al. Human cytomegalovirus UL23 inhibits transcription of interferon-gamma stimulated genes and blocks antiviral interferon-gamma responses by interacting with human N-myc interactor protein. *PLoS Pathog.* 2018; 14(1):e1006867). Upregulation of NMI in the presence of cytokines such as TNF-α has been shown to retard cell migration and invasion. (Hou J, Wang T, Xie Q, et al. N-Myc-interacting protein (NMI) negatively regulates epithelial-mesenchymal transition by inhibiting the acetylation of NF-kappaB/p65. *Cancer Lett.* 2016; 376(1):22-33; Hou J, Jiang S, Zhao J, et al. N-Myc-Interacting Protein Negatively Regulates TNFalpha-Induced NF-kappaB Transcriptional Activity by Sequestering NF-kappaB/p65 in the Cytoplasm. *Sci Rep.* 2017; 7(1):14579). However, the role of NMI in regulation of pathologic EMT in chronic lung diseases including CLAD is yet unknown. Likewise, the impact of the lung microbiome in alterations of NMI and mediation of EMT response in the lung has not been evaluated previously.

In light of the shortcomings of the prior art, what is needed is the delineation of potential biomarkers for therapeutics in treating, diagnosing or preventing chronic lung inflammation or CLAD. In particular, biomarkers allowing for early diagnosis of CLAD are needed.

SUMMARY OF INVENTION

The inventors identified N-myc-interactor (NMI) as a critical regulator of epithelial-mesenchymal transition (EMT), an important precursor to CLAD development. The inventors investigated the distinct airway microbiome in CLAD subjects compared to those without CLAD and investigated the roles for NMI in microbiome induced EMT and human CLAD. The inventors found that a Proteobacteria dominant lung microbiome inhibits NMI expression and induces epithelial to mesenchymal transition (EMT) which correlates with CLAD. Thus, CLAD is associated with increased bacterial biomass and a Proteobacteria enriched airway microbiome and EMT. Exposure of human primary bronchial epithelial cells to *Pseudomonas aeruginosa* (PsA) resulted in downregulation of NMI and induction of an EMT phenotype. Upregulation of NMI expression favorably modulates EMT expression to attenuate the PsA-induced EMT response.

The invention has multiple potential applications as a biomarker for early diagnosis, as a pharmaceutic target, and for delivery as recombinant protein or gene therapy as treatment. Hence N-myc-interactor (NMI) protein, or the gene encoding it, can be used in many forms.

In one embodiment, NMI can be used as an early diagnostic biomarker to predict the development of epithelial-mesenchymal transition (EMT) and chronic lung diseases including CLAD in lung transplant patients. In this embodiment, a method of predicting and treating development of chronic lung allograft dysfunction (CLAD) in a patient in need thereof is presented comprising: obtaining a sample from the patient; obtaining an expression level of N-myc-interactor (NMI) protein or gene in the sample; comparing the expression level of the NMI protein or gene in the sample to a control; wherein decreased expression of NMI protein or gene as compared to the control indicates the development of CLAD; and administering a therapeutically effective amount of a therapeutic agent if development of CLAD is indicated.

The therapeutic agent may be selected from the group consisting of antibiotics, neomacrolides, montelukast, pirfenidone, nintedanib, alemtuzamab, immunosuppressants, and an NMI modulator composition.

The therapeutic agent may be an NMI modulator composition comprising nanoparticles coated with NMI recombinant protein and a pharmaceutically acceptable carrier. Alternatively, the therapeutic agent may be an NMI modulator composition comprising nanoparticles coated with expression vector or with messenger RNA encoding the NMI gene and a pharmaceutically acceptable carrier.

In another embodiment, NMI can be used as a novel drug target to augment NMI protein reduction in patients with chronic lung diseases or pulmonary transplantation to reduce onset of EMT and development of CLAD. In this embodiment, a method of reducing risk of developing chronic lung allograft dysfunction (CLAD) in a patient in need thereof is presented comprising administering a therapeutically effective amount of a therapeutic agent to increase an expression level of N-myc-interactor (NMI) in the patient wherein the increase in NMI reduces the risk of the CLAD development in the patient.

The therapeutic agent may be an antibiotic targeted to genus Proteobacteria, specifically *Pseudomonas aeruginosa*. The antibiotic may be administered prior to and/or after a lung transplant.

The therapeutic agent may be a composition comprising NMI recombinant protein, such as a composition comprising a plurality of NMI recombinant protein-coated nanoparticles and a pharmaceutically acceptable carrier. The therapeutic agent may be administered intranasally after a lung transplant.

Alternatively, the therapeutic agent may be a composition comprising a plurality of nanoparticles coated with NMI gene expression vector or NMI gene messenger RNA. The composition may be administered after a lung transplant.

In a further embodiment, NMI can be used as a therapeutic recombinant NMI protein that could be delivered to patients with chronic lung diseases or pulmonary transplantation, for example by, but not limited to, inhaling of nanoparticles coated with NMI protein. Alternatively, NMI can be used as a therapeutic for gene therapy using nanoparticles coated with an expression vector or messenger RNA that encodes the NMI gene or viral gene therapy for NMI gene airway delivery.

A method of treating chronic lung allograft dysfunction (CLAD) in a patient in need thereof is presented comprising administering a therapeutically effective amount of a therapeutic agent to increase an expression level of N-myc-interactor (NMI) in the patient.

The therapeutic agent may be a composition comprising NMI protein or an NMI expression vector and a pharmaceutically acceptable carrier. In some embodiments, the composition may comprise a plurality of NMI protein-coated nanoparticles administered intranasally. In other embodiments, the composition may comprise a plurality of nanoparticles coated with NMI gene expression vector.

BRIEF DESCRIPTION OF THE DRAWINGS

For a fuller understanding of the invention, reference should be made to the following detailed description, taken in connection with the accompanying drawings, in which.

*P<0.05, P<0.01, *P<0.001, unpaired T test (vimentin, NMI, E-cadherin, SMAD 2,3, ZO-1, SLUG, SNAIL), Mann-Whitney test (TGF-β1 and N-cadherin).

FIG. 8A-C are a series of images depicting gene expression of EMT markers (A) E-cadherin, (B) N-cadherin and (C) NMI in freshly collected CLAD and non(N)-CLAD subjects, n=4 each group. All expression levels are normalized to GAPDH. Error bars represent mean±SEM. The level of significance was indicated by *P<0.05, P<0.01, *P<0.001.

FIG. 9A-D are a series of images depicting *Pseudomonas aeruginosa* downregulates NMI and induces EMT and in primary bronchial epithelial cells. (A) PBECs were exposed to PsA with a mode of infectivity of 1:1 for a period of 16 hours. The expression of NMI and the EMT markers N-cadherin, vimentin and E-cadherin was evaluated by Western blot analysis. (B) Densitometric analysis of independent experiments (n=3) performed as in (A) represents the quantitative protein expression/GAPDH. (C) PBECs were exposed to PsA-LPS at a concentration of 100 μg/ml for a period of 48 hours. The expression of EMT transcriptional factors SLUG and ZO-1 were evaluated by Western blotting. (D) Densitometric analysis of independent experiments (n=3) performed in (C) represents the quantitative protein expression/GAPDH. Error bars represent mean+/−SEM. The level of significance is indicated by *P<0.05, P<0.01, *P<0.001, unpaired T test for all comparisons.

Figure 10:
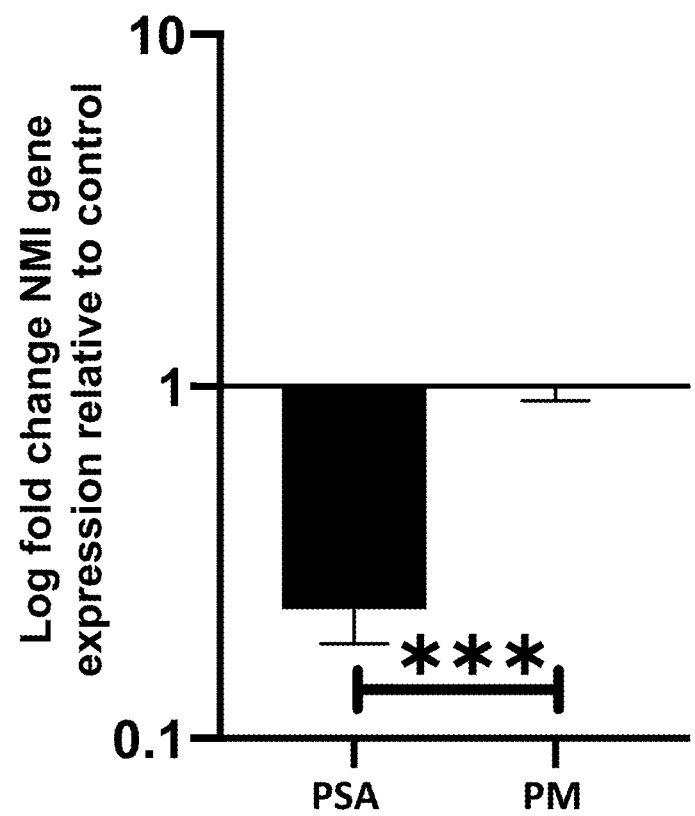

FIG. 10 is a graph depicting NMI gene expression differences in PsA or PM (*Prevotella melaninogenica*) exposed PBECs. PBECs were exposed to PsA or PM with a mode of infectivity of 1:1 for a period of 16 hours. Error bars showing mean±SEM, ***P<0.001.

Figure 11:
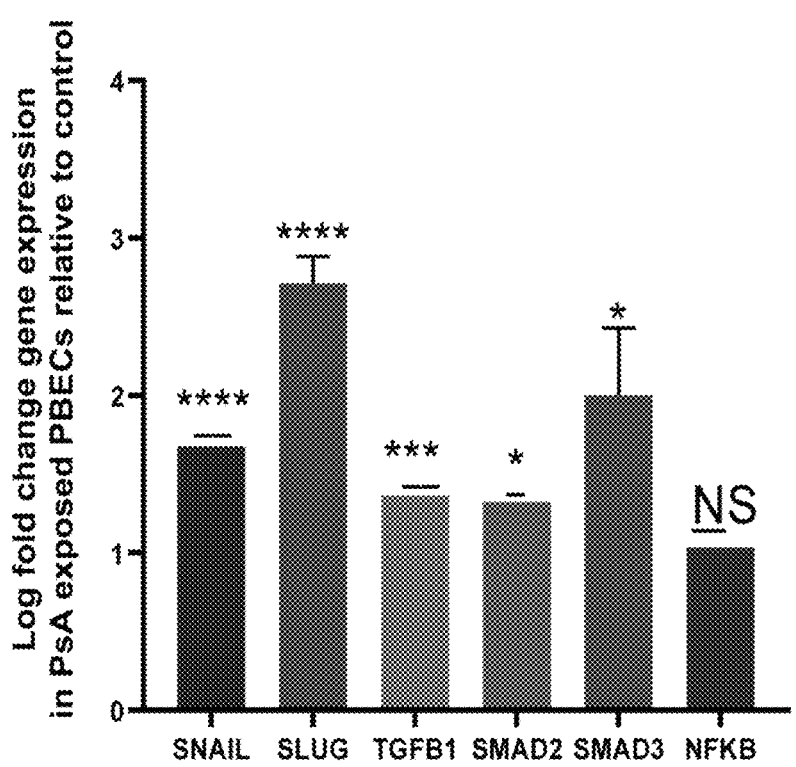

FIG. 11 is a graph depicting transcript levels of NMI is reduced in PsA exposed PBECs. PBECs were exposed to PsA-LPS at a concentration of 100 μg/ml for a period of 48 hours. (A) Quantitative analysis of transcript levels of EMT transcriptional factors (SLUG/SNAIL), the TGF-β/SMAD pathway players (SMAD2/3 and SMAD7) and NF-κB P65 of the NF-κB pathway were assayed by qRT-PCR. All expression levels are normalized to GAPDH. Fold change values were done with respect to control samples using Livak method. Error bars represent mean+/−SEM. The level of significance is indicated by *P<0.05, P<0.01, *P<0.001.

FIG. 12A-B are a series of graphs depicting NMI regulates EMT in primary bronchial epithelial cells. (A) NMI was silenced or overexpressed in PBECs, respectively, and its expression along with that of EMT markers N-cadherin, vimentin and E-cadherin was evaluated by Western blotting. (B) Densitometric analysis of independent experiments (n=3) performed as in (A) represents the quantitative protein expression/GAPDH of EMT markers N-cadherin, vimentin and E-cadherin with respect to either silencing or overexpression of NMI, respectively. Both the NMI siRNA and NMI overexpression data were normalized to scrambled siRNA. Error bars represent mean±SEM. The level of significance is indicated by *P<0.05, P<0.01, *P<0.001., unpaired T test for all comparisons.

Figure 13:
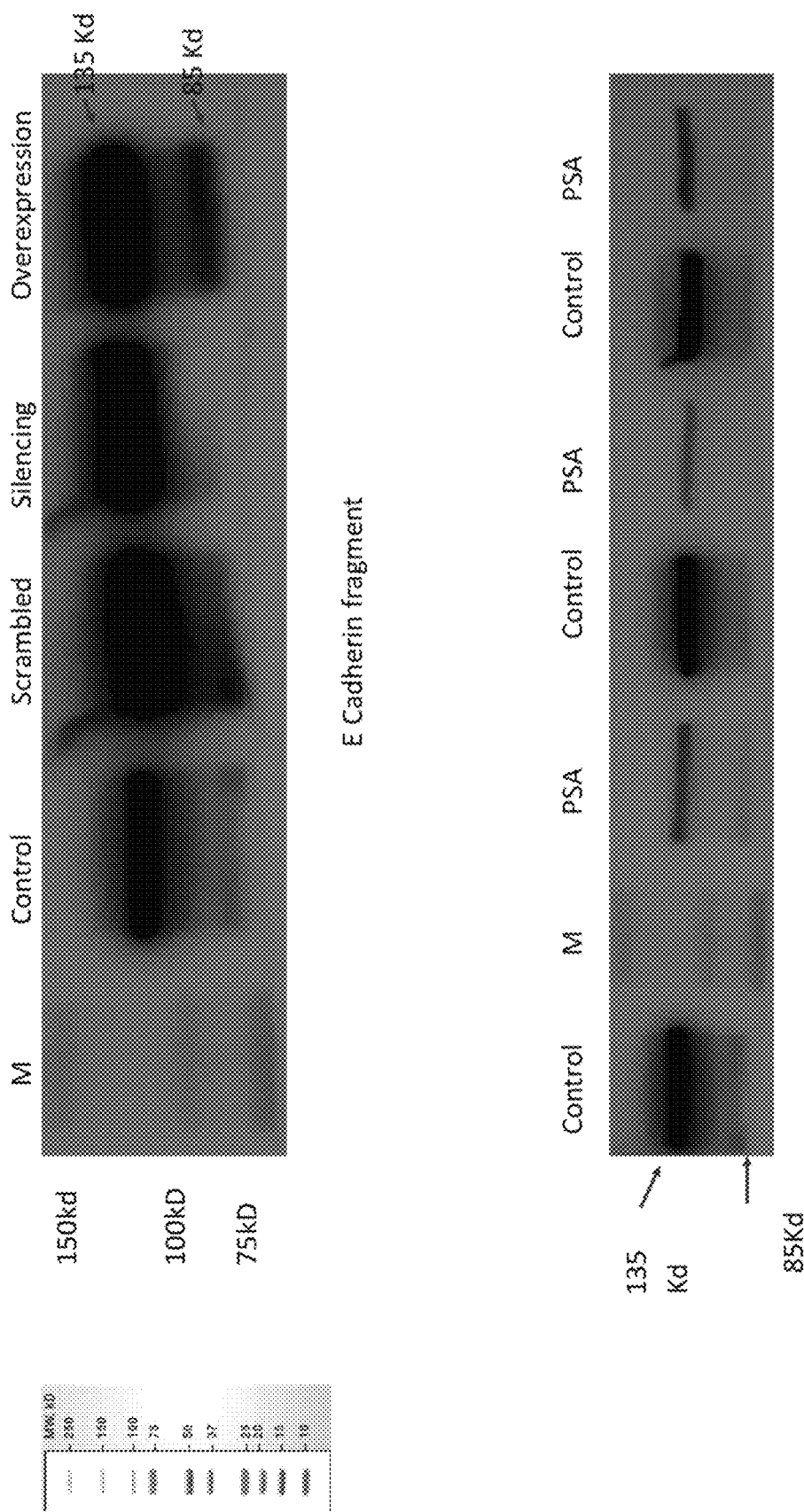

FIG. 13 is a series of Western blots with ladder showing E-cadherin expression in control, scrambled siRNA, NMI siRNA and NMI overexpressed experiment. Two bands associated with E-cadherin are identified in the experiments. The full-length E-cadherin protein (135 kD) and a minor fragment (85 kD) which runs between 75 and 100 kDa markers. The relative proportion of the lower band (85 kD) is low and is seen in normal conditions or in conditions where NMI is overexpressed.

Figure 14:
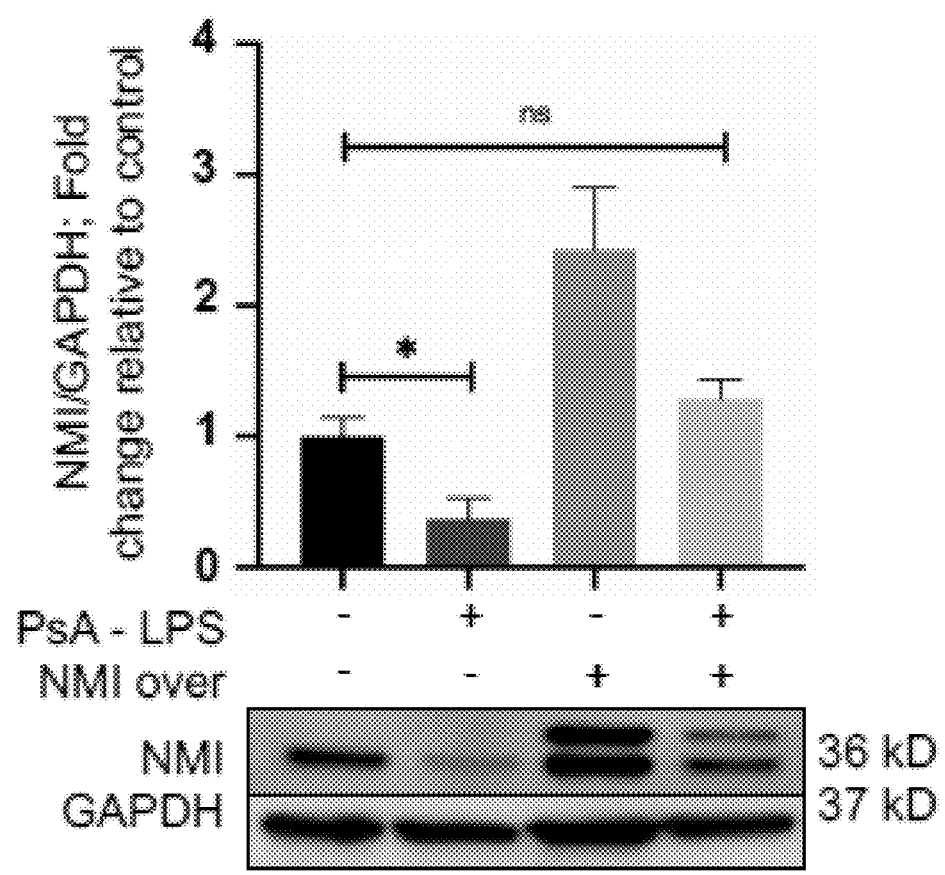

FIG. 14 is a series of images depicting PsA-LPS downregulates NMI in PBECs. PBECs and PBECs overexpressed with NMI were exposed to PsA-LPS at a concentration of 100 μg/ml for a period of 48 hours. The expression of NMI was evaluated by Western blotting. Densitometric analysis of independent experiments (n=3) represents the quantitative protein expression/GAPDH. Error bars represent mean+/−SEM. The level of significance is indicated by *P<0.05, P<0.01, *P<0.001.

Figure 15:
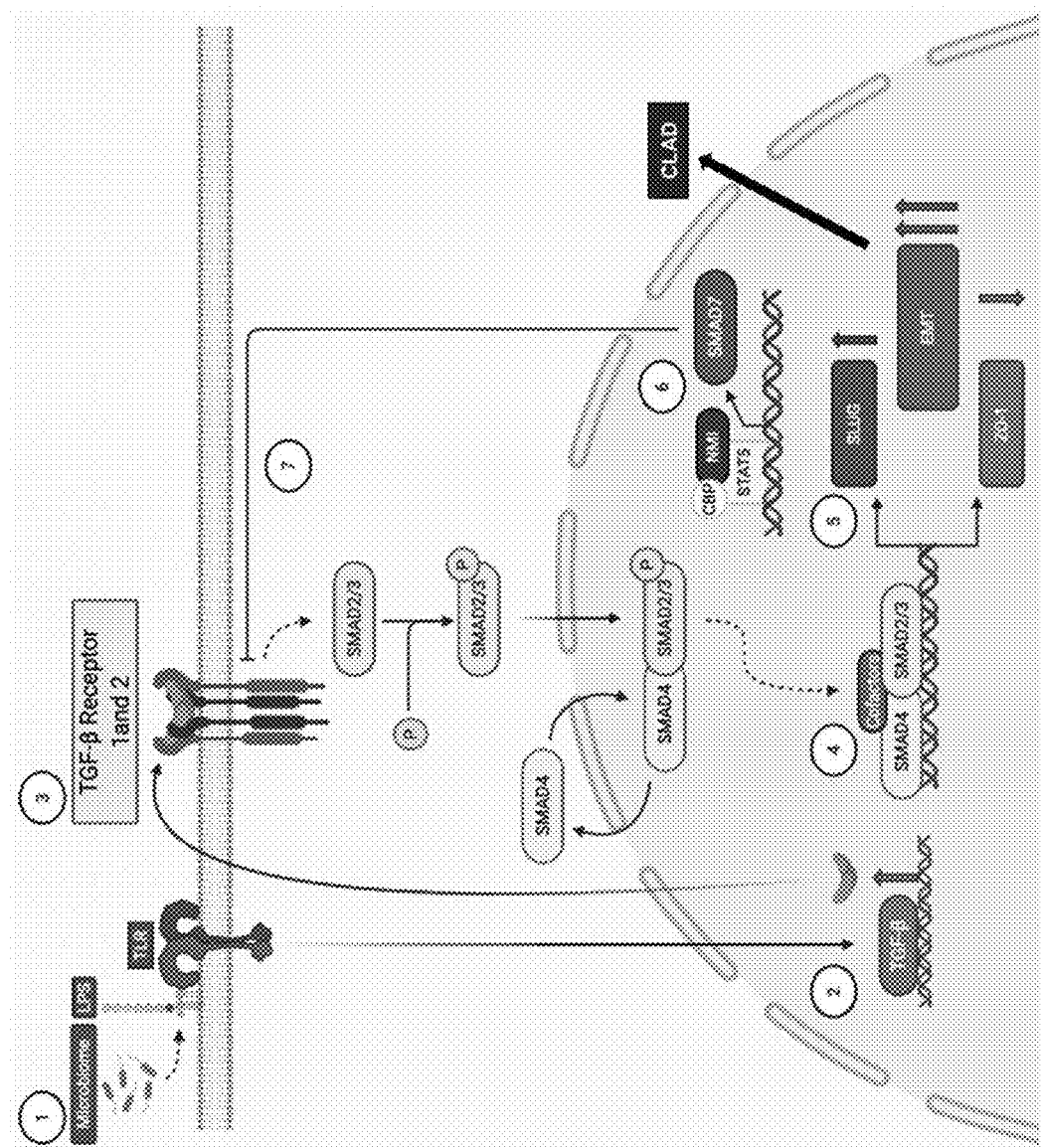

FIG. 15 is an image depicting a model of *Pseudomonas aeruginosa* (PsA)/LPS-induced signaling in the lung resulting in EMT and CLAD. (1) PsA/LPS via TLR signaling induces upregulation of TGF-β in pulmonary bronchial epithelial cells. TGF-β is secreted by PBECs (2) and in turn in an autocrine manner (3) acts via TGF-β receptor to activate TGF-β/SMAD signaling. SMAD2/3 is phosphorylated and enters the nucleus and in combination with other cofactors (4) of the transcriptional machinery induces EMT by modulating the expression of EMT transcription factors SLUG (SNAI2) and ZO-1 (5). NMI on account of being an IFN-7 responsive gene is downregulated by TGF-β (6). Downregulation of NMI removes the inhibitory effect of SMAD7 on TGF-β/SMAD signaling (7) and thus enhancing EMT and CLAD (8).

DETAILED DESCRIPTION OF THE PREFERRED EMBODIMENT

In the following detailed description of the preferred embodiments, reference is made to the accompanying drawings, which form a part hereof, and within which are shown by way of illustration specific embodiments by which the invention may be practiced. It is to be understood that other embodiments may be utilized, and structural changes may be made without departing from the scope of the invention.

Abbreviations

BAL—bronchoalveolar lavage
CF—cystic fibrosis
CLAD—chronic lung allograft dysfunction
EMT—epithelial-to-mesenchymal transition
LPS—lipopolysaccharide
NMI—N-myc interactor
PsA—*Pseudomonas aeruginosa*

Definitions

Unless otherwise defined, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are described herein. All publications mentioned herein are incorporated herein by reference in their entirety to disclose and describe the methods and/or materials in connection with which the publications are cited. It is understood that the present disclosure supercedes any disclosure of an incorporated publication to the extent there is a contradiction.

As used herein, the singular forms "a," "an" and "the" include plural referents unless the context clearly dictates otherwise.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include the individual values and sub-ranges within the indicated range, to the tenth of the unit. Thus, included in this numerical range are individual values such as 2, 3, and 4 and sub-ranges such as from 1-3, from 2-4 and from 3-5, etc. This same principle applies to ranges reciting only one numerical value. Furthermore, such an interpretation should apply regardless of the range or the characteristics being described.

All numerical designations, including ranges, are approximations which are varied up or down by increments of 1.0, 0.1 or 0.01, as appropriate. It is to be understood, even if it is not always explicitly stated that all numerical designations are preceded by the term "about". It is also to be understood, even if it is not always explicitly stated, that the reagents described herein are merely exemplary and that equivalents of such are known in the art and can be substituted for the reagents explicitly stated herein.

As used herein, the term "comprising" is intended to mean that the products, compositions, and methods include the referenced components or steps, but not excluding others. "Consisting essentially of" when used to define products, compositions, and methods, shall mean excluding other components or steps of any essential significance. "Consisting of" shall mean excluding more than trace elements of other components or steps.

"Optional" or "optionally" means that the subsequently described event or circumstance may or may not occur, and that the description includes instances where said event or circumstance occurs and instances where it does not.

The term "about" or "approximately" as used herein refers to being within an acceptable error range for the particular value as determined by one of ordinary skill in the art, which will depend in part on how the value is measured or determined. As used herein, the term "about" refers to ±10%.

"Patient" is used to describe an animal, preferably a mammal, more preferably a human, to whom treatment is administered, including prophylactic treatment with the compositions of the present invention. "Patient" and "subject" are used interchangeably herein.

The term "biomarker" is used herein to refer to a molecule whose level of nucleic acid or protein product has a quantitatively differential concentration or level with respect to an aspect of a biological state of a subject. "Biomarker" is used interchangeably with "marker" herein. The level of the biomarker can be measured at both the nucleic acid level as well as the polypeptide level. At the nucleic acid level, a nucleic acid gene or a transcript which is transcribed from any part of the subject's chromosomal and extrachromosomal genome, including for example the mitochondrial genome, may be measured. Preferably an RNA transcript, more preferably an RNA transcript includes a primary transcript, a spliced transcript, an alternatively spliced transcript, or an mRNA of the biomarker is measured. At the polypeptide level, a pre-propeptide, a propeptide, a mature peptide or a secreted peptide of the biomarker may be measured. A biomarker can be used either solely or in conjunction with one or more other identified biomarkers so as to allow correlation to the biological state of interest as defined herein. Specific examples of biomarkers covered by the present invention include genes involved in cell cycle regulation, specifically epithelial-to-mesenchymal transition (EMT). More specifically, biomarkers of the present invention include N-myc-interactor (NMI).

The term "biological state" as used herein refers to the result of the occurrence of a series of biological processes. As the biological processes change relative to each other, the biological state also changes. One measurement of a biological state is the level of activity of biological variables such as biomarkers, parameters, and/or processes at a specified time or under specified experimental or environmental conditions. A biological state can include, for example, the state of an individual cell, a tissue, an organ, and/or a multicellular organism. A biological state can be measured in samples taken from a normal subject or a diseased subject thus measuring the biological state at different time intervals may indicate the progression of a disease in a subject. The biological state may include a state that is indicative of disease (e.g. diagnosis); a state that is indicative of the progression or regression of the disease (e.g. prognosis); a state that is indicative of the susceptibility (risk) of a subject to therapy for the disease or of the disease itself; and a state that is indicative of the efficacy of a treatment of the disease.

The genes of the present invention may serve as biomarkers for: (1) the diagnosis of disease; (2) the prognosis of diseases (e.g. monitoring disease progression or regression from one biological state to another); (3) the susceptibility or prediction of response to treatment for a disease; or (4) the evaluation of the efficacy to a treatment for disease. For the diagnosis of disease, the level of the specific gene in the subject can be compared to a baseline or control level in which if the level is above the control level, a certain disease is implicated. The prognosis of disease can be assessed by comparing the level of the specific gene biomarker at a first timepoint to the level of the biomarker at a second timepoint which occurs at a given interval after the first timepoint. The prediction of response to treatment for a disease can be determined by obtaining the level of a specific gene biomarker and correlating this level to an overall senescence score. The evaluation of the efficacy of the treatment for a disease can be assessed by comparing the level of the specific gene biomarker at a first timepoint before administration of the treatment to the level of the biomarker at a second timepoint which occurs at a specified interval after the administration of the treatment.

The term "expression level" as used herein refers to detecting the amount or level of expression of a biomarker of the present invention. The act of actually detecting the expression level of a biomarker refers to the act of actively determining whether a biomarker is expressed in a sample or not. This act can include determining whether the biomarker expression is upregulated, downregulated or substantially unchanged as compared to a control level expressed in a sample. The expression level in some cases may refer to detecting transcription of the gene encoding a biomarker protein and/or to detecting translation of the biomarker protein.

Expression of genes/transcripts and/or polypeptides encoded by the genes represented by the biomarkers of the present invention can be measured by any of a variety of methods known in the art. In general, expression of a nucleic acid molecule (e.g. RNA or DNA) can be detected by any suitable method or technique of measuring or detecting gene or polynucleotide sequence or expression. Such methods include, but are not limited to, polymerase chain reaction (PCR), reverse transcriptase PCR (RT-PCR), in situ PCR, quantitative PCR (q-PCR), quantitative RT-PCR (qRT-PCR), in situ hybridization, Southern blot, Northern blot, sequence analysis, microarray analysis, detection of a reporter gene, or any other DNA/RNA hybridization platforms.

The term "baseline level" or "control level" of biomarker expression or activity refers to the level against which biomarker expression in the test sample can be compared. In some embodiments, the baseline level can be a normal level, meaning the level in a sample from a normal patient. This allows a determination based on the baseline level of biomarker expression or biological activity, whether a sample to be evaluated for disease cell growth has a measurable increase, decrease, or substantially no change in biomarker expression as compared to the baseline level. The term "negative control" used in reference to a baseline level of biomarker expression generally refers to a baseline level established in a sample from the subject or from a population of individuals which is believed to be normal. In other embodiments, the baseline level can be indicative of a positive diagnosis of disease (e.g., positive control). The term "positive control" as used herein refers to a level of biomarker expression or biological activity established in a sample from a subject, from another individual, or from a population of individuals, where the sample was believed, based on data from that sample, to have the disease. In other embodiments, the baseline level can be established from a previous sample from the subject being tested, so that the disease progression or regression of the subject can be monitored over time and/or the efficacy of treatment can be evaluated.

The term "quantifying" or "quantitating" when used in the context of quantifying transcription levels of a gene can refer to absolute or relative quantification. Absolute quantification can be achieved by including known concentration(s) of one or more target nucleic acids and referencing the hybridization intensity of unknowns with the known target nucleic acids (e.g., through the generation of a standard curve). Alternatively, relative quantification can be achieved by comparison of hybridization signals between two or more genes, or between two or more treatments to quantify the changes in hybridization intensity and, by implication transcription level.

Methods to measure protein/polypeptide expression levels of selected biomarkers in the present invention include, but are not limited to: Western blot, immunoblot, enzyme-linked immunosorbent assay (ELISA), radioimmunoassay (RIA), immunoprecipitation, surface plasmon resonance, chemiluminescence, fluorescent polarization, phosphorescence, immunohistochemical analysis, liquid chromatography mass spectrometry (LC-MS), matrix-assisted laser desorption/ionization time-of-flight (MALDI-TOF), mass spectrometry, microcytometry, microarray, microscopy, fluorescence activated cell sorting (FACS), flow cytometry, and assays based on a property of the protein including but not limited to DNA binding, ligand binding, or interaction with other protein partners.

The term "gene expression product" or "expression product" as used herein refers to an RNA transcribed from a gene (either pre- or post-processing) or an amino acid (e.g. a polypeptide, protein, or peptide regardless of any secondary modifications, such as glycosylation, lipidation or phosphorylation) encoded by the gene and generated by the gene when the gene is transcribed (either pre- or post-modification) and translated. An agent is said to increase gene expression if the application of a therapeutically effective amount of the agent to a cell or subject results in an increase in either an RNA or polypeptide expression product or both. An agent is said to decrease gene expression if the application of a therapeutically effective amount of the agent to a cell or subject results in a decrease in either an RNA or polypeptide expression product or both.

The term "polynucleotide" as used herein refers to a polymeric molecule that has a backbone that supports bases capable of hydrogen bonding to typical polynucleotides. The polymer backbone presents the bases in a manner that is effective to allow such hydrogen bonding in a sequence specific fashion between the polymeric molecule and a typical polynucleotide, such as single-stranded DNA. Polymeric molecules include both single and double stranded DNA or RNA and can include polymers having backbone modifications. It includes the recited sequences as well as their complementary sequences, which can be easily ascertained by those of ordinary skill in the art.

An "isolated polynucleotide" as used herein refers to a polynucleotide which is separated from other nucleic acid molecules which are present in the natural source of the polynucleotide. Preferably, an "isolated polynucleotide" is free of sequences which naturally flank the polynucleotide in the genomic DNA of the organism from which the nucleic acid is derived. An "isolated polynucleotide" is substantially free of other cellular material, gel materials, and culture medium when produced by recombinant techniques, or substantially free of chemical precursors or other chemicals when chemically synthesized. The polynucleotides of the present invention may be isolated from a variety of sources, such as PCR amplification from genomic DNA, mRNA, or cDNA libraries derived from the mRNA using standard techniques.

The term "nucleic acid" as used herein may be double-stranded, single-stranded, or contain portions of both double and single stranded sequence. If the nucleic acid is single-stranded, the sequence of the other strand is also identifiable and thus the definition includes the complement of the sequence disclosed. "Nucleic acid" includes one or more types of: polydeoxyribonucleotides (containing 2-deoxy-D-ribose), polyribonucleotides (containing D-ribose), and any other type of polynucleotide that is an N-glycoside of a purine or pyrimidine base, or modified purine or pyrimidine bases (including abasic sites). The term "nucleic acid," as used herein, also includes polymers of ribonucleosides or deoxyribonucleosides that are covalently bonded, typically by phosphodiester linkages between subunits, but in some cases by phosphorothioates, methylphosphonates, and the like. "Nucleic acids" include single- and double-stranded DNA, as well as single- and double-stranded RNA. Exemplary nucleic acids include, without limitation, gDNA; hnRNA; mRNA; rRNA, tRNA, micro RNA (miRNA), small interfering RNA (siRNA), small nucleolar RNA (snORNA), small nuclear RNA (snRNA), and small temporal RNA (stRNA), and the like, and any combination thereof.

The term "polypeptide" as used herein refers to a compound made up of a single chain of amino acid residues that are linked by peptide bonds. The term "protein" may be synonymous with the term "polypeptide" or may refer, in addition, to a complex of two or more polypeptides. Generally, polypeptides and proteins are formed predominantly of naturally occurring amino acids. As used herein, terms including, but not limited to "peptide," "dipeptide," "tripeptide," "protein," "enzyme," "amino acid chain," and "contiguous amino acid sequence" are all encompassed within the definition of a "polypeptide," and the term "polypeptide" can be used instead of, or interchangeably with, any of these terms. The term further includes polypeptides that have undergone one or more post-translational modification(s), including for example, but not limited to, glycosylation, acetylation, phosphorylation, amidation, derivatization, proteolytic cleavage, post-translation processing, or modification by inclusion of one or more non-naturally occurring amino acids.

The term "differential expression" as used herein refers to qualitative or quantitative differences in the temporal and/or spatial gene expression patterns within and among cells and tissues. A differentially expressed gene may qualitatively have its expression altered, including an activation or inactivation, such as in normal versus diseased tissue. Genes may be turned off or on in a given state relative to another state thus allowing comparison of two or more states. A qualitatively regulated gene may exhibit an expression pattern within a state or cell type that can be detectable by standard techniques. Alternatively, the difference in expression may be quantitative such that expression of the gene is modulated, up-regulated (resulting in an increased amount of transcript), or down-regulated (resulting in a decreased amount of transcript). The degree to which expression varies needs to be large enough to quantify via standard characterization techniques such as expression arrays, quantitative reverse transcriptase PCR, Northern blot analysis, real-time PCR, in situ hybridization, and RNase protection.

The term "expression profile" as used herein refers to a genomic expression profile. The profiles may be generated by any means for determining a level of a nucleic acid sequence, e.g. quantitative hybridization of microRNA, labeled microRNA, amplified microRNA, cDNA, quantitative PCR, ELISA for quantitation, etc. For proteins, the profiles may be generated by any means for determining a level of a protein, e.g. Western blot, immunoblot, enzyme-linked immunosorbent assay (ELISA), radioimmunoassay (RIA), immunoprecipitation, surface plasmon resonance, chemiluminescence, fluorescent polarization, phosphorescence, immunohistochemical analysis, liquid chromatography mass spectrometry (LC-MS), matrix-assisted laser desorption/ionization time-of-flight (MALDI-TOF), mass spectrometry, microcytometry, microarray, microscopy, fluorescence activated cell sorting (FACS), flow cytometry, and assays based on a property of the protein including but not limited to DNA binding, ligand binding, or interaction with other protein partners. The profile must allow for the analysis of differential gene expression between two samples.

The terms "overexpression" and "underexpression" as used herein refers to the expression of a gene of a patient at a greater or lesser level, respectively, than the normal or control expression of the gene, as measured by gene expression product expression such as mRNA or protein expression, in a sample that is greater than the standard of error of the assay used to assess the expression. A "significant" expression level may be a level which either meets or is above or below a predetermined score for a gene.

"Sample," as used herein, refers to a any physical sample that includes a cell or a cell extract from a cell, a tissue, or an organ including a biopsy sample. In some embodiments, the sample is a composition that is obtained or derived from a subject and/or individual of interest that contains a cellular and/or other molecular entity that is to be characterized and/or identified, for example, based on physical, biochemical, chemical, and/or physiological characteristics. The sample can be from a biological source such as a subject or animal, or a portion thereof, or can be from a cell culture. Samples from a biological source can be from a normal or an abnormal organism, such as an organism known to be suffering from a condition or a disease state such as a neoplasm, or any portion thereof. Samples can also be from any fluid, tissue or organ including normal and abnormal (diseased or neoplastic) fluid, tissue or organ. Samples from a subject or animal can be used in the present invention as obtained by the subject or animal and processed or cultured such that cells from the sample can be sustained in vitro as a primary or continuous cell culture or cell line.

"Tissue sample" or "cell sample" is meant a collection of similar cells obtained from a tissue of a subject or individual. The source of the tissue or cell sample may be solid tissue as from a fresh, frozen and/or preserved organ, tissue sample, biopsy, and/or aspirate; blood or any blood constituents such as plasma; bodily fluids; cells from any time in gestation or development of the subject. The tissue sample may also be primary or cultured cells or cell lines. Optionally, the tissue or cell sample is obtained from a disease tissue/organ.

A "reference sample," "reference cell," "reference tissue," "control sample," "control cell," or "control tissue," as used herein, refers to a sample, cell, tissue, standard, or level that is used for comparison purposes. In one embodiment, a reference sample, reference cell, reference tissue, control sample, control cell, or control tissue is obtained from a healthy and/or non-diseased part of the body (e.g., tissue or cells) of the same subject or individual. For example, the reference sample, reference cell, reference tissue, control sample, control cell, or control tissue may be healthy and/or non-diseased cells or tissue adjacent to the diseased cells or tissue (e.g., cells or tissue adjacent to a tumor). In another embodiment, a reference sample is obtained from an untreated tissue and/or cell of the body of the same subject or individual. In yet another embodiment, a reference sample, reference cell, reference tissue, control sample, control cell, or control tissue is obtained from a healthy and/or non-diseased part of the body (e.g., tissues or cells) of an individual who is not the subject or individual. In even another embodiment, a reference sample, reference cell, reference tissue, control sample, control cell, or control tissue is obtained from an untreated tissue and/or cell of the body of an individual who is not the subject or individual.

The term "cell" or "cells" is used synonymously herein and refers to in vitro cultures of mammalian cells grown and maintained as known in the art, as well as biological samples obtained from disease specimens or normal specimens in vivo.

"Pharmaceutically acceptable carrier" means any of the standard pharmaceutically acceptable carriers. The pharmaceutically acceptable carrier can include diluents, adjuvants, and vehicles, as well as implant carriers, and inert, non-toxic solid or liquid fillers, diluents, or encapsulating material that does not react with the active ingredients of the invention. Examples include, but are not limited to, phosphate buffered saline, physiological saline, water, and emulsions, such as oil/water emulsions. The carrier can be a solvent or dispersing medium containing, for example, ethanol, polyol (for example, glycerol, propylene glycol, liquid polyethylene glycol, and the like), suitable mixtures thereof, and vegetable oils. Formulations are described in a number of sources that are well known and readily available to those skilled in the art. For example, *Remington's Pharmaceutical Sciences* (Martin E W [1995] Easton Pennsylvania, Mack Publishing Company, 19$^{th}$ ed.) describes formulations which can be used in connection with the subject invention. In some embodiments, phosphate buffered saline is used as the pharmaceutically acceptable carrier.

The terms "administer" or "administering" as used herein are defined as the process by which the compositions of the present invention are delivered to the patient for treatment, diagnostic or prevention purposes. The composition can be delivered via any suitable means including, but not limited to, parenteral, oral and intranasally, in dosage unit formulations containing conventional nontoxic pharmaceutically acceptable carriers, adjuvants, and vehicles as desired. Parenteral infusions include, for example, intramuscular, intravenous, intraarterial, intraperitoneal, or subcutaneous administration. Intranasal administration includes, but is not limited to, bronchoalveolar lavage and aerosol sprays. In bronchoalveolar lavage, the bronchoscope may be passed either through the mouth or the nose. Various dosing schedules including but not limited to single or multiple administrations over various timepoints, bolus administration, and pulse infusion are contemplated herein.

"Therapeutic agent" as used herein is defined as a substance, component or agent that has measurable specified or selective physiological activity when administered to an individual in a therapeutically effective amount. Examples of therapeutic agents as used in the present invention include compositions, drugs, genes, gene products, beneficial bacteria, and antimicrobials such as antibiotics. Specific exemplary therapeutic agents include, but are not limited to, antibiotics, neomacrolides, leukotriene modifiers such as montelukast, pirfenidone, nintedanib, alemtuzumab, immunoglobulins, rituximab, immunosuppressants, NMI amplifiers, bronchodilators, steroids, phosphodiesterase-4 inhibitors, theophylline, CF transmembrane conductance regulator (CFTR) modulators, and combinations thereof. Antibiotics useful herein include, but are not limited to, antibiotics against the phylum Proteobacteria, genera *Pseudomonas*, including, but not limited to, Gram-negative bacteria such as *P. aeruginosa* infections. Such antibiotics include, but are not limited to, aminoglycosides (e.g., gentamicin, tobramycin, amikacin, netilmicin); carbapenems (imipenem, meropenem); cephalosporins (ceftazidime, cefepime); fluoroquinolones (ciprofloxacin, levofloxacin); penicillin with β-lactamase inhibitors (BLI) (ticarcillin and piperacillin in combination with clavulanic acid or tazobactam); monobactams (aztreonam); Fosfomycin; and polymyxins (colistin, polymyxin B). At least one therapeutic agent is used in the compositions of the present invention. In some embodiments, multiple therapeutic agents are used and are released in a sequential manner. In some embodiments, the therapeutic agents are administered intranasally (inhaled or through bronchoalveolar lavage).

"Beneficial bacteria" as used herein refers to bacteria that confers or promotes health benefits to the patient. Examples of beneficial bacteria in the lung microbiome useful herein include, but are not limited to, bacteria in phylum Bacteroidetes, bacteria in genera *Prevotella*, bacteria in phylum Actinobacteria, bacteria in phylum Fusobacteria. Examples of beneficial bacteria may also include lung microbiome collected from healthy donors and people without CLAD, for example by bronchoalveolar lavage. An increase in phylum Proteobacteria is associated with chronic lung disease. As such, bacteria in this phylum would not be considered beneficial bacteria with respect to the lung microbiome.

A "therapeutically effective amount" as used herein is defined as concentrations or amounts of components which are sufficient to effect beneficial or desired clinical results, including, but not limited to, any one or more of treating symptoms of chronic lung disease. Compositions of the present invention can be used to effect a favorable change in the condition whether that change is an improvement or a complete elimination of symptoms due to chronic lung disease. In accordance with the present invention, a suitable single dose size is a dose that is capable of preventing or alleviating (reducing or eliminating) a symptom in a subject when administered one or more times over a suitable time period. One of skill in the art can readily determine appropriate single dose sizes for systemic administration based on the size of the animal and the route of administration. The therapeutically effective amount of the compositions of the present invention encompasses providing treatment or enhancing treatment without causing significant side effects or adverse reactions.

"Diagnosing" or "diagnosis" as used herein refers to the identification or classification of a molecular or pathological state, disease or condition (e.g., chronic lung disease). For example, "diagnosis" may refer to identification of a particular type of chronic lung disease. "Diagnosis" may also refer to the classification of a particular subtype of chronic lung disease, for instance by histopathological criteria or by molecular features (e.g., a subtype characterized by expression of one or a combination of biomarkers).

The term "prognosis" refers to the determination or prediction of the course of disease or condition or to monitoring disease progression or regression from one biological state to another. Prognosis can include the determination of the time course of a disease, with or without treatment. Where treatment is included, the prognosis includes determining the efficacy of the treatment for the disease or condition.

The terms "risk or susceptibility" as used herein refers to the determination as to whether a subject would or would not respond to a particular therapy or would or would not develop a particular disease or symptom.

"Prevention" or "preventing" as used herein refers to any of: halting the effects of chronic lung disease; reducing the effects of chronic lung disease; reducing the incidence of chronic lung disease; reducing the development of chronic lung disease; delaying the onset of symptoms of chronic lung disease; increasing the time to onset of symptoms of chronic lung disease; and reducing the risk of development of chronic lung disease.

"Treatment" or "treating" as used herein refers to any of the alleviation, amelioration, elimination and/or stabilization of a symptom, as well as delay in progression of a symptom of a particular disorder. For example, "treatment" may include any one or more of the following: amelioration and/or elimination of one or more symptoms associated with chronic lung disease; reduction of one or more symptoms of chronic lung disease; stabilization of symptoms of chronic lung disease; and delay in progression of one or more symptoms of chronic lung disease. "Treatment" as used herein is meant to encompass prophylactic treatment.

"Composition" as used herein refers to a product comprising the specified ingredients in the specified amounts, as well as any product which results, directly or indirectly, from combination of the specified ingredients in the specified amounts. In some embodiments, the composition includes both the therapeutic agent as well as one or more pharmaceutically acceptable carriers. In some embodiments, the composition is present as a solution containing at least one therapeutic agent that is capable of parenteral, intranasal or oral administration.

"Nanoparticle" as used herein refers to a particle or structure which is biocompatible with and sufficiently resistant to chemical and/or physical destruction by the environment of such use so that a sufficient number of the nanoparticles remain substantially intact after delivery to the site of application or treatment and whose size is in the nanometer range. Use of nanoparticles allows for sustained release of the therapeutic agent. For the purposes of the present invention, a nanoparticle typically ranges between about 1 nm to about 1000 nm, preferably between about 50 nm and about 500 nm, more preferably between about 50 nm and about 350 nm, more preferably between about 100 nm and about 250 nm. As used herein, the term "nanoparticle" includes, but is not limited to, micelles, dendrimers, polymeric nanoparticles, aggregates, inorganic nanoparticles, and lipid-based nanoparticles such as liposomes, solid lipid nanoparticles (SLN), nanostructured lipid carriers (NLC), and niosomes.

In some embodiments, NMI protein may be coated on, conjugated to, or encapsulated within the nanoparticles for delivery with a pharmaceutically acceptable carrier as a composition to treat, even prophylactically, a chronic lung disease, such as CLAD, characterized by a decrease in NMI. In other embodiments, NMI gene may be encoded by an expression vector which is coated on or encapsulated within the nanoparticles for delivery with a pharmaceutically acceptable carrier as a composition to treat, including prophylactically, a chronic lung disease, such as CLAD, characterized by a decrease in NMI. In yet other embodiments, NMI gene may be encoded by messenger RNA (mRNA), or chemical modifications thereof, which is coated on or encapsulated within the nanoparticles for delivery with a pharmaceutically acceptable carrier as a composition to treat, including prophylactically, a chronic lung disease, such as CLAD, characterized by a decrease in NMI.

"Vector" as used herein refers to a nucleic acid molecule (typically comprised of DNA) capable of expressing a gene of interest in a host cell, which may or may not be capable of replication in a host cell and/or to which another nucleic acid segment can be operatively linked so as to bring about replication of the attached segment. A plasmid, cosmid, or a virus is an exemplary vector. "Vector" and "expression vector" are used interchangeably herein. In some embodiments, the vector comprises a nucleic acid sequence encoding for NMI operatively linked to a promotor and capable of expressing NMI in a suitable host cell of the patient.

The term "promoter," as used herein refers to a region or regions of a nucleic acid sequence that regulates transcription.

"Chronic lung disease" as used herein refers to diseases of the airways or other structures of the lung which lead to long-term breathing problems. Symptoms include, but are not limited to, shortness of breath, wheezing, chronic coughing, reduced airflow, and difficulty breathing. Examples of chronic lung diseases that may be treated or diagnosed herein include, but are not limited to, chronic lung allograft dysfunction (CLAD); cystic fibrosis (CF); chronic obstructive pulmonary disorder (COPD); emphysema; chronic bronchitis; interstitial lung diseases such as idiopathic pulmonary fibrosis (IPF) and bronchiolitis obliterans; severe asthma; and/or bronchiectasis. As used herein, chronic lung diseases capable of being treated, prevented or diagnosed by the instant invention include those which are characterized by a decrease in NMI.

"NMI modulator" as used herein refers to a composition or therapeutic agent comprised of NMI protein or NMI gene that, when administered to a patient, increases the expression of NMI (protein or gene). In some embodiments, the NMI modulator is a composition of nanoparticles having the NMI protein (recombinant or otherwise) or NMI gene (encoded by an expression vector) coated on, conjugated to, or encapsulated within the nanoparticles. The composition may also include a pharmaceutically acceptable carrier.

Lung transplant remains the primary treatment option for patients with advanced lung disease or irreversible pulmonary failure, including chronic obstructive pulmonary disease (COPD), severe asthma, cystic fibrosis or idiopathic pulmonary fibrosis. COPD alone independently affects more than 3 million US patients per year and cystic fibrosis affects about 200,000 US cases per year. Unfortunately, long term survival of lung transplant recipients is the lowest among all other solid organ transplants. Although, survival rates for lung transplant recipients have improved, the major obstacle limiting longer survival in these patients is the development of chronic lung allograft dysfunction (CLAD) or chronic rejection. Currently, there are no biomarkers to detect CLAD at an earlier timepoint and the treatment for CLAD has limited efficacy. Hence early diagnosis of the development of CLAD is critical as it affords early intervention that may improve survival of these patients.

Recent evidence suggests a role for lung microbiome in occurrence of chronic lung allograft dysfunction (CLAD). However, the mechanisms linking microbiome to CLAD are not delineated. The inventors investigated the mechanisms involved in microbial modulation of mucosal response leading to CLAD and hypothesized that a Proteobacteria, specifically a Gammaproteobacteria, dominant lung microbiome alters NMI expression, induces epithelial to mesenchymal transition (EMT) and correlates with CLAD. Upregulation of NMI expression would favorably modulate EMT expression. The inventors report the distinct airway microbiome in CLAD subjects compared to those without CLAD and investigate the regulatory role of NMI in microbiome induced EMT and CLAD.

The inventors have identified N-myc-interactor (NMI) as a critical regulator of epithelial-mesenchymal transition (EMT), an important precursor to CLAD development. Tissue samples obtained from explant human CLAD lungs and control lungs were compared for expression levels of epithelial marker E-cadherin and mesenchymal markers vimentin, alpha-SMA and N-cadherin, together with gene and protein expression levels of NMI. Western blot analysis and qRT-PCR was performed to evaluate EMT in lung explants from CLAD and matched non-CLAD transplant patients. The results showed a significant reduction of gene and protein expression levels of E-cadherin, together with an upregulation of the mesenchymal markers vimentin, alpha-SMA and N-cadherin in patients with CLAD compared to controls. Moreover, the inventors showed significant downregulation of NMI gene and protein expression levels in patients that had developed CLAD which correlated with airway EMT.

Additionally, human primary bronchial epithelial cells (PBEC) were co-cultured with the lung bacterium *Pseudomonas aeruginosa* for 24 hours. This induced an EMT phenotype as evidenced by downregulation of E-cadherin and upregulation of vimentin, alpha-SMA and N-cadherin in PBEC cultures, as shown before in the CLAD patients with EMT. Similar to the CLAD explant results, gene and protein expression of NMI was significantly reduced in PBECs that underwent EMT due to exposure to *Pseudomonas aeruginosa*. These experiments were repeated after NMI downregulation by small interfering RNA (siRNA) and upregulation by plasmid vector in PBECs transfected with NMI siRNA or overexpression vector, which confirmed NMI as a critical regulator of airway EMT.

The present invention provides a novel biomarker for early diagnosis of the development of epithelial-mesenchymal transition (EMT) and chronic lung diseases including CLAD in lung transplant patients.

Also provided is the use of NMI as a novel target for a therapeutic drawn to treating patients with chronic lung diseases such as CLAD. Furthermore, NMI can be used as a target for reducing the risk of a patient developing CLAD.

Further, the present invention provides use of NMI gene or protein as a novel therapeutic that can be delivered to patients with chronic lung diseases or pulmonary transplantation. The therapeutic can be in different forms and generally comprises administering NMI protein or NMI gene to increase NMI in the patient. If administering NMI protein, the protein may be a recombinant protein. In an exemplary embodiment, the NMI protein may be administered intranasally via a composition comprising coated nanoparticles. Alternatively, the composition may be administered parenterally or orally. The protein may be conjugated to the surface of the nanoparticles or alternatively may be encapsulated within the nanoparticles for efficient delivery.

If administering the NMI gene, an expression vector or messenger RNA (mRNA) encoding the NMI gene may be used for administration. In some embodiments, the vector may be administrated parenterally, orally, or intranasally. In some embodiments, the NMI expression vector or mRNA may be administered in a pharmaceutically acceptable carrier or alternatively, the NMI expression vector or mRNA may be coated onto nanoparticles in a pharmaceutically acceptable carrier which are then administered as a composition to the patient.

Nanoparticles have been used to deliver proteins, vectors and various other therapeutics to the lungs via oral, parenteral (intravenous) and intranasal administrations. (Buxton, D. B., Nanomedicine for the management of lung and blood diseases, *nanomedicine (Lond.)*, 2009 April; 4(3):331-339). Exemplary carrier matrix materials include, but are not limited to, chitosan; polyethyleneimine (PEI); poly(lactic-co-glycolic acid) (PLGA); polyamidoamine; stearic acid; silica; palmitic acid; poly(glycerol adipate-co-ω-pentadecalactone) (PGA-co-PDL); palmitic acid; glyceryl behenate; cholesteryl myristate; and oleic acid as noted in Pontes, J. F., et al., herein incorporated by reference into this disclosure. (Pontes, J. F., et al., Multifunctional nanocarriers for lung drug delivery, *Nanomaterials*, 2020; 10(2):183-207). One of skill in the art can determine the optimal formulation for the optimal carrier type and matrix materials according to the type of molecule being encapsulated within, coated onto or conjugated to the nanoparticle.

The following non-limiting examples illustrate exemplary systems and components thereof in accordance with various embodiments of the disclosure. The examples are merely illustrative and are not intended to limit the disclosure in any way. While the examples are drawn to CLAD, other chronic lung diseases are contemplated as being diagnosed and/or treated with the invention described herein.

Example 1—NMI as a Biomarker for CLAD

The inventors characterized distinct microbiome signatures in CLAD subjects and identified possible mechanisms linking microbiome to CLAD pathogenesis. The results showed that subjects with CLAD have a higher abundance of phylum Proteobacteria and reduced abundance of the phylum Bacteroidetes. At the genera level, CLAD subjects had an increased abundance of *Pseudomonas* and reduced genera *Prevotella*. Furthermore, human CLAD airway cells were characterized by downregulation of the gene N-myc-interactor (NMI) and presence of epithelial to mesenchymal transition (EMT).

The inventors are the first to present clear mechanistic data linking Proteobacteria exposure (*Pseudomonas aeruginosa* (PsA)) with downregulation of NMI and induction of an EMT phenotype. The importance of this signaling axis is further validated by demonstrating that NMI upregulation resulted in attenuation of this PsA-induced EMT response. These data provide a new pathway of tissue injury, active in CLAD and laying the foundation for longitudinal studies to further investigate the utility of specific microbiome signatures in risk stratification for CLAD susceptibility. Importantly, this new signaling pathway is likely operative in other chronic airway disorders with Proteobacteria colonization such as cystic fibrosis, COPD and bronchiectasis.

Previous studies using culture-based techniques have reported that *Pseudomonas* infection and/or colonization is associated with occurrence of CLAD. (Botha P, Archer L, Anderson R L, et al. *Pseudomonas aeruginosa* colonization of the allograft after lung transplantation and the risk of bronchiolitis obliterans syndrome. *Transplantation*. 2008; 85(5):771-774; Nakajima T, Palchevsky V, Perkins D L, Belperio J A, Finn P W. Lung transplantation: infection, inflammation, and the microbiome. *Semin Immunopathol*. 2011; 33(2):135-156). The inventors used culture-independent techniques and found that subjects with CLAD had a higher abundance of the phylum Proteobacteria and a lower abundance of Bacteroidetes. At the genera level, these translated to an increased abundance of the genus *Pseudomonas* and reduced genus *Prevotella, Haemophilus* and *Neisseria* in the CLAD lungs compared to non-CLAD groups. Interestingly, two species of *Streptococcus* had differential abundance in CLAD and non-CLAD with *Streptococcus* 516966 higher in non-CLAD, while *Streptococcus* 2024840 increased in CLAD.

The inventors have previously reported that a shift from a Firmicute dominant to a Proteobacteria dominant microbiome is associated with CLAD. (Sharma N S, Wille K M, Athira S, et al. Distal airway microbiome is associated with immunoregulatory myeloid cell responses in lung transplant recipients. *The Journal of heart and lung transplantation: the official publication of the International Society for Heart Transplantation*. 2017; 37(2):P206). The current results are concordant with some of these observations and provide more granular genus level airway microbial signature differences in CLAD compared to non-CLAD subjects.

In addition to these, the airway bacterial biomass in the CLAD cohort was noted to be significantly higher than the non-CLAD cohort. Reduced community diversity and a higher bacterial count are indicative of microbial dysbiosis. (Petersen C, Round J L. Defining dysbiosis and its influence on host immunity and disease. *Cell Microbiol*. 2014; 16(7): 1024-1033). Likewise, the microbial dysbiosis index in CLAD was altered compared to non-CLAD suggesting increased dysbiosis in CLAD. Several studies have shown that increased gut bacterial dysbiosis correlates to onset and progression of chronic systemic diseases. Lung microbial dysbiosis has been linked to progression of COPD and IPF. (O'Dwyer D N, Ashley S L, Gurczynski S J, et al. Lung Microbiota Contribute to Pulmonary Inflammation and Disease Progression in Pulmonary Fibrosis. *American journal of respiratory and critical care medicine*. 2019; 199(9): 1127-1138; Dickson R P, Huang Y J, Martinez F J, Huffnagle G B. The lung microbiome and viral induced exacerbations of chronic obstructive pulmonary disease: new observations, novel approaches. *American journal of respiratory and critical care medicine.* 2013; 188(10):1185-1186).

More recently, a study reported that dysbiosis with Actinobacteria reduced microbiome with abundance of gram-negative bacteria such as *Pseudomonas* and *Flavobacterium* is associated with worse outcomes in lung transplant recipients while that enriched with Actinobacteria and *Streptococcus* are protective from CLAD. (Schott C, Weigt S S, Turturice B A, et al. Bronchiolitis obliterans syndrome susceptibility and the pulmonary microbiome. *The Journal of heart and lung transplantation: the official publication of the International Society for Heart Transplantation.* 2018; 37(9):1131-1140). Currently, it is not known if lung dysbiosis or the increase in airway Proteobacteria abundance predates CLAD or a result of the decreased bacterial clearance by a fibrotic CLAD airway. Future longitudinal microbiome studies are needed to shed light on the temporal association of the alterations in the airway microbiome with development of CLAD.

CLAD phenotypes are characterized by dense airway and/or parenchymal fibrosis leading to reduced allograft function. (Belperio J A, Lake K, Tazelaar H, Keane M P, Strieter R M, Lynch J P, 3rd. Bronchiolitis obliterans syndrome complicating lung or heart-lung transplantation. *Seminars in respiratory and critical care medicine.* 2003; 24(5):499-530; Belperio J A, Weigt S S, Fishbein M C, Lynch J P, 3rd. Chronic lung allograft rejection: mechanisms and therapy. *Proceedings of the American Thoracic Society.* 2009; 6(1):108-121). Previous studies have indicated that CLAD is associated with epithelial-to-mesenchymal transition (EMT). (Borthwick L A, Parker S M, Brougham K A, et al. Epithelial to mesenchymal transition (EMT) and airway remodelling after human lung transplantation. *Thorax.* 2009; 64(9):770-777; Renaud-Picard B, Valliere K, Toussaint J, et al. Epithelial-mesenchymal transition and membrane microparticles: Potential implications for bronchiolitis obliterans syndrome after lung transplantation. *Transpl Immunol.* 2020; 59:101273). During EMT, epithelial cells lose their tight junction markers like E-cadherin accompanied by an increase in the expression of mesenchymal markers such as N-cadherin (increases cell migration potential), vimentin, smooth muscle actin and fibronectin. (Rout-Pitt N, Farrow N, Parsons D, Donnelley M. Epithelial mesenchymal transition (EMT): a universal process in lung diseases with implications for cystic fibrosis pathophysiology. *Respir Res.* 2018; 19(1):136).

Although EMT can be physiological response to stress and injury, dysregulation can lead to pathological changes including tissue fibrosis. (Bartis D, Mise N, Mahida R Y, Eickelberg O, Thickett D R. Epithelial-mesenchymal transition in lung development and disease: does it exist and is it important? *Thorax.* 2014; 69(8):760-765; Salton F, Volpe M C, Confalonieri M. Epithelial-Mesenchymal Transition in the Pathogenesis of Idiopathic Pulmonary Fibrosis. *Medicina (Kaunas).* 2019; 55(4)). The findings from explant CLAD airway cells validated the presence of EMT and downregulation of the NMI gene in CLAD. NMI is a signaling transduction protein and transcriptional regulator that has been shown to modulate tumor invasion and metastasis in several cancers. (Feng X, Xu X, Xiao X, et al. NMI inhibits cancer stem cell traits by downregulating hTERT in breast cancer. *Cell Death Dis.* 2017; 8(5):e2783; Hou J, Wang T, Xie Q, et al. N-Myc-interacting protein (NMI) negatively regulates epithelial-mesenchymal transition by inhibiting the acetylation of NF-kappaB/p65. *Cancer Lett.* 2016; 376(1):22-33; Hou J, Jiang S, Zhao J, et al. N-Myc-Interacting Protein Negatively Regulates TNFalpha-Induced NF-kappaB Transcriptional Activity by Sequestering NF-kappaB/p65 in the Cytoplasm. *Sci Rep.* 2017; 7(1):14579).

Figure 12:
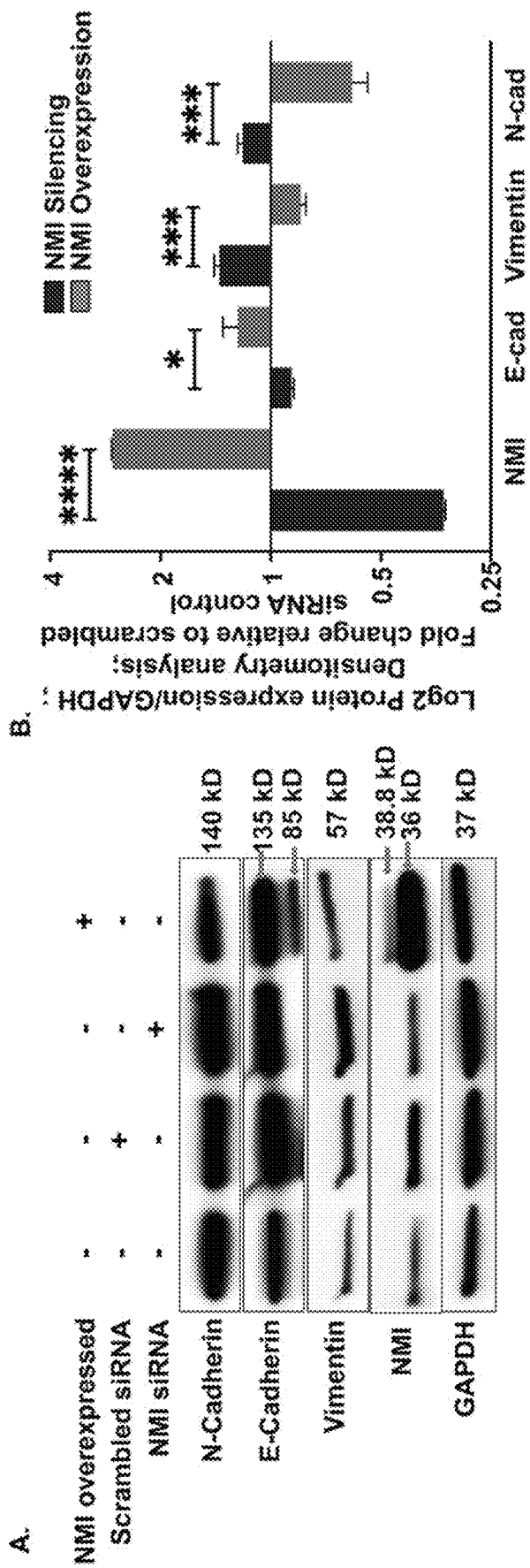

Several pathways such as the p65-NF-κB-ZEB2 and TGF-SMAD pathways are known to regulate EMT. (Bartis D, Mise N, Mahida R Y, Eickelberg O, Thickett D R. Epithelial-mesenchymal transition in lung development and disease: does it exist and is it important? *Thorax.* 2014; 69(8):760-765; Rout-Pitt N, Farrow N, Parsons D, Donnelley M. Epithelial mesenchymal transition (EMT): a universal process in lung diseases with implications for cystic fibrosis pathophysiology. *Respir Res.* 2018; 19(1):136). The mechanistic studies show that NMI regulates EMT in human primary bronchial epithelial cells (FIG. 12). NMI downregulation is known to activate TGF-SMAD-STAT and the p65-NF-κB-ZEB2 axis leading to EMT. (Devine D J, Rostas J W, Metge B J, et al. Loss of N-Myc interactor promotes epithelial-mesenchymal transition by activation of TGF-beta/SMAD signaling. *Oncogene.* 2014; 33(20):2620-2628). The in vitro experiments demonstrate that upregulation of NMI in primary human bronchial epithelial cells (PBECs) attenuated the EMT responses, while partial siRNA blockade enhanced the EMT phenotype. In the human CLAD cohort, the TGFβ/SMAD pathway was upregulated suggesting a possible role in EMT and fibrogenesis leading to CLAD.

Tissue injury, hypoxia states, and toxins can activate an EMT response. (Choi B J, Park S A, Lee S Y, Cha Y N, Surh Y J. Hypoxia induces epithelial-mesenchymal transition in colorectal cancer cells through ubiquitin-specific protease 47-mediated stabilization of Snail: A potential role of Sox9. *Sci Rep.* 2017; 7(1):15918; Kalluri R, Weinberg R A. The basics of epithelial-mesenchymal transition. *J Clin Invest.* 2009; 119(6):1420-1428). Likewise, viruses such as EBV and Hepatitis (B and C) can induce EMT. (Bose S K, Meyer K, Di Bisceglie A M, Ray R B, Ray R. Hepatitis C virus induces epithelial-mesenchymal transition in primary human hepatocytes. *J Virol.* 2012; 86(24):13621-13628; Morris M A, Laverick L, Wei W, et al. The EBV-Encoded Oncoprotein, LMP1, Induces an Epithelial-to-Mesenchymal Transition (EMT) via Its CTAR1 Domain through Integrin-Mediated ERK-MAPK Signalling. *Cancers (Basel).* 2018; 10(5):130). Moreover, bacterial products such as LPS and flagellin may also trigger an EMT response. (Hofman P, Vouret-Craviari V. Microbes-induced EMT at the crossroad of inflammation and cancer. *Gut Microbes.* 2012; 3(3):176-185; Jing Y Y, Han Z P, Sun K, et al. Toll-like receptor 4 signaling promotes epithelial-mesenchymal transition in human hepatocellular carcinoma induced by lipopolysaccharide. *BMC Med.* 2012; 10:98).

Figure 9:
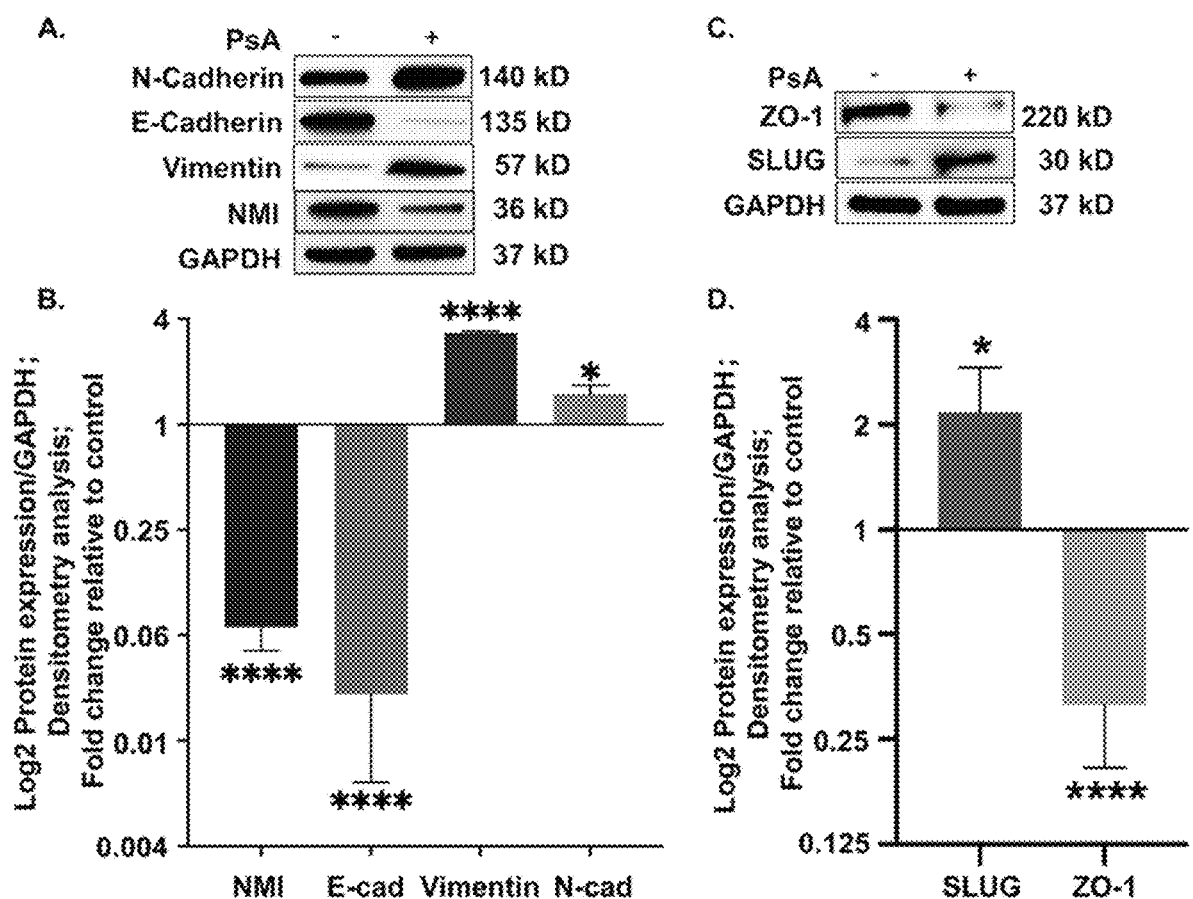

In order to establish the link between microbiome and EMT in bronchiolitis obliterans syndrome CLAD (BOS-CLAD), the inventors investigated whether the *Pseudomonas aeruginosa* (PsA), a bacterium with enhanced abundance in CLAD-altered NMI expression, triggered an EMT response in PBECs. The inventors found that exposure to PsA or LPS upregulated expression of mesenchymal markers vimentin and N-cadherin and downregulated E-cadherin suggesting an EMT phenotype. (FIG. 9)

Furthermore, expression of NMI was significantly reduced in PsA/LPS-exposed PBECs, thus validating a role for bacteria in modulation of EMT via NMI downregulation. To determine whether NMI, in part, regulated PsA-induced EMT in PBECs, the inventors exposed NMI-overexpressing PBECs to PsA-LPS. Upregulation of NMI expression dampened the EMT response suggesting a possible mediatory role for NMI in PsA-induced EMT. NMI has been previously evaluated as a therapeutic target to mitigate metastatic potential in several cancers. (Pruitt H C, Metge B J, Weeks S E, et al. Conditional knockout of N-Myc and STAT interactor disrupts normal mammary development and enhances metastatic ability of mammary tumors. *Oncogene*. 2018; 37(12):1610-1623; Wang J, Zou K, Feng X, et al. Downregulation of NMI promotes tumor growth and predicts poor prognosis in human lung adenocarcinomas. *Mol Cancer.* 2017; 16(1):158). Here, the inventors provide a mechanistic link between the lung microbiome and pathogenesis of CLAD. Animal transplantation models can be used to validate and test the therapeutic potential of NMI in reducing risk of CLAD.

The study has subjects from a single center in the southeast US. Center variations in the choices of post-transplant antibiotic prophylaxis, levels of immunosuppression and environmental factors may all affect the microbiome. Nevertheless, a moderate sample size and previous validation of some of the findings in an independent cohort previously support the validity of the observations. The inventors found NMI expression to be downregulated in explant CLAD lungs and in PsA exposed PBECs, however there may be other triggers that alter NMI expression. Likewise, microbiome may mediate EMT and CLAD onset via other alternate pathways. Future studies evaluating microbiome in CLAD and investigating the role of BMI in CLAD need to be conducted to study these aspects in greater detail.

Although the CLAD and non-CLAD groups were aged matched and overall similar in terms of immunosuppression and prophylactic antibiotics; BAL culture positivity rate and mean time from transplantation was higher in the CLAD subjects compared to the non-CLAD group. Likewise, due to the cross-sectional nature and lack of pretransplant microbiome data for the subjects in the study, the inventors cannot determine whether the lung microbiome is donor or recipient derived. A recent study showed distinct microbiome in the native and transplanted lungs of single lung transplant recipients thus suggesting that the post-lung transplant microbiome may be donor derived. (Sharma N S, Vestal G, Wille K, et al. Differences in airway microbiome and metabolome of single lung transplant recipients. *Respir Res.* 2020; 21(1):104).

Figure 8:
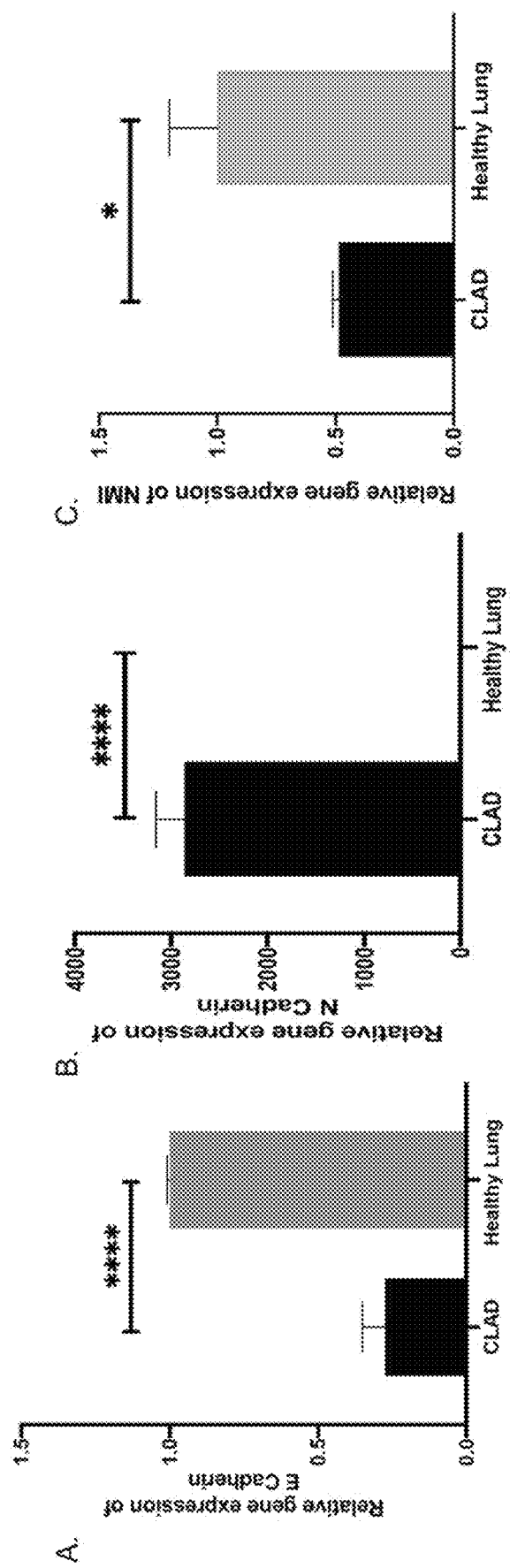

The gene expressions observed in the autopsy human CLAD and non-CLAD specimens were confirmed with similar gene expression profiles noted in freshly collected and processed explant CLAD lung tissues (FIG. 8). The inventors evaluate the impact of pre and post-transplant Proteobacterial colonization in cystic fibrosis (CF) lung transplant recipients on the host-microbiome immune interaction.

Results

Gene/protein expression of mesenchymal markers vimentin (V), α-SMA (A), N-cadherin (N) were elevated and epithelial marker E-cadherin (E), NMI significantly reduced in explant CLAD compared to controls. 16S rRNA analysis of CLAD BAL showed reduced bacterial diversity (Shannon index, p=0.01), increased bacterial biomass (16S gene copy/ml BAL, P=0.04) and a predominance of class Gammaproteobacteria (p=0.03) and genus *Pseudomonas* (p=0.01) compared to matched non-CLAD controls. PBEC exposure to PsA resulted in increased expression of V, N, A and significant reduction in E suggesting EMT. Expression of NMI was significantly reduced in PsA-exposed PBECs. PsA exposure in NMI-overexpressed PBECs attenuated EMT and in NMI-downregulated PBECs augmented EMT.

Figure 1:
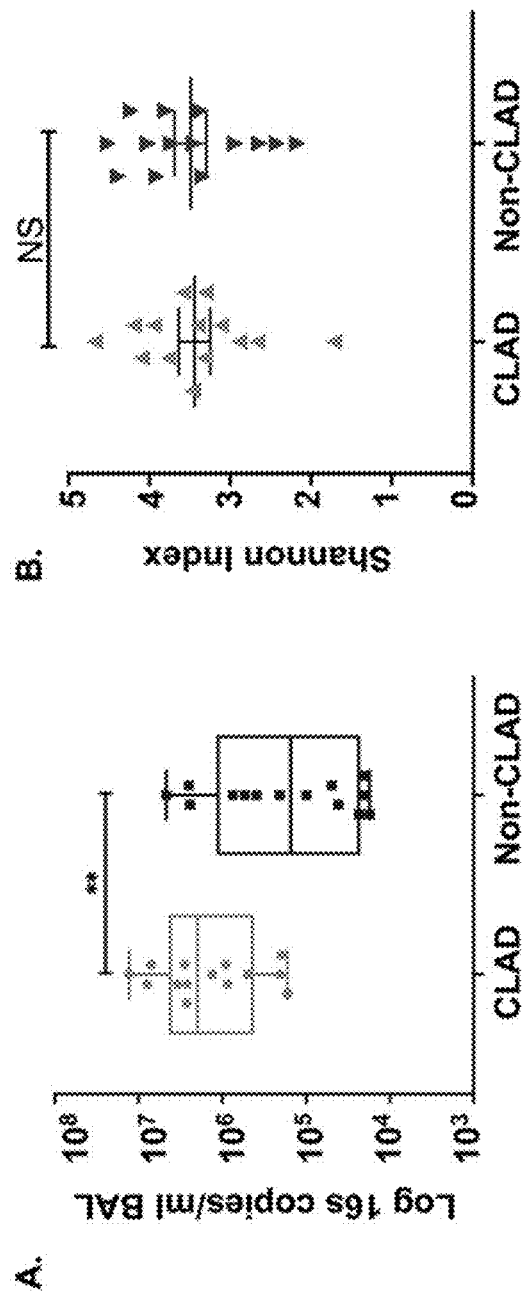
FIG. 1A-B are a series of graphs depicting bacterial biomass and alpha diversity in BAL of CLAD and non-CLAD subjects. (A) Box plot showing bacterial 16S gene copies/ml BAL in CLAD versus non-CLAD lung transplant recipients. The box signifies the upper (Q3) and lower quartiles (Q1), and the median is represented by a line within the box. All individual data points are shown. ** $P=0.006$ (n=14), Mann-Whitney test. (B) Shannon diversity index in CLAD versus non-CLAD lung transplant recipients. Error bars showing mean±SEM, P=NS (not significant), unpaired T test, (n=14).

The CLAD BAL Lung Microbiome has a Higher Bacterial Biomass Compared to Non-CLAD The inventors first determined the bacterial biomass in CLAD versus the non-CLAD BAL specimens using 16S quantitative PCR. The overall bacterial biomass in CLAD was significantly higher compared to the non-CLAD group $(2.77 \times 10^6$ vs $7.6 \times 10^5$ per ml BAL, P=0.006) (FIG. 1**A). In order to determine whether the CLAD and non-CLAD groups differed in diversity of bacterial communities between BAL specimens, the inventors calculated the Shannon diversity index as a measure of α-diversity within a sample that represents both species richness and evenness. (Li K, Bihan M, Yooseph S, Methe B A. Analyses of the microbial diversity across the human microbiome. *PLoS One.* 2012; 7(6):e32118). No significant difference was seen in the Shannon diversity index of CLAD compared to non-CLAD groups (3.44 vs 3.49, P=0.8) (FIG. 1B).

Figure 2:
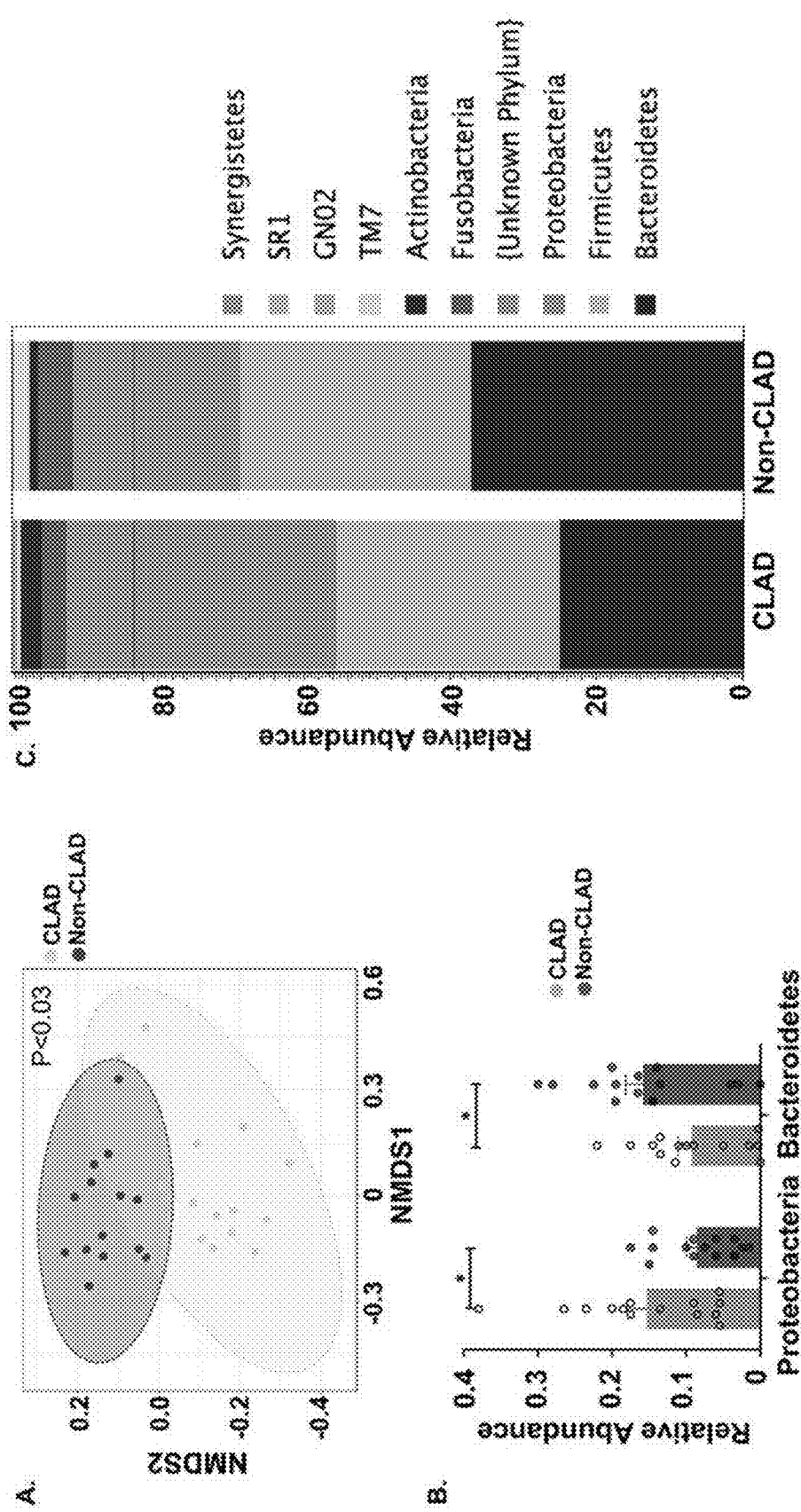
FIG. 2A-C is a series of images depicting BAL microbiome of CLAD and non-CLAD. (A) Nonmetric multi-dimensional scaling (NMDA) plot showing Bray-Curtis distance between CLAD and Non-CLAD airway microbiome in lung transplant recipients. CLAD are shown in the lower circled cluster and non-CLAD in the upper circled cluster. P value calculated via PERMANOVA analysis CLAD vs non-CLAD, $P<0.03$. NMDS stress value of −0.1 (n=14). (B) Relative abundance of phyla Proteobacteria and Bacteroidetes in CLAD and non-CLAD subjects (n=14). Error bars showing mean±SEM, *$P<0.05$, unpaired T test. (C) Phyla level composition of bacterial operational taxonomic units (OTUs) in CLAD and non-CLAD subjects.

CLAD Airways have a Higher Abundance of Proteobacteria and Lower Abundance of Bacteroidetes Compared to Non-CLAD To determine the BAL lung microbiome in the CLAD and non-CLAD cohorts, we performed 16S rRNA gene amplicon analyses. Using Bray-Curtis distance metric, the NMDS plot showed a wide separation of the CLAD and non-CLAD groups (P<0.03, PERMANOVA) (FIG. 2A). Next, we investigated the phyla level taxonomic differences between the groups. The abundance of phylum Proteobacteria was significantly higher, while that of phylum Bacteroidetes significantly lower in CLAD compared to non-CLAD (FIG. 2B, 2C). Abundance of phylum Firmicutes was similar between the groups. At the genera level, the abundance of *Pseudomonas* (Gammmaproteobacteria) was significantly higher in CLAD, while that of genus *Prevotella* (Bacteroidetes) significantly higher in the non-CLAD group (Table 1). Likewise, *Streptococcus* 516966, *Fusobacterium, Haemophilus,* and *Neisseria* were significantly enriched in non-CLAD compared to CLAD. Details of the genera level differences with maximum group mean of at least 1000 between the two groups are presented in Table 1.

TABLE 1

Details of genera level differences enriched in CLAD compared to non-CLAD

| Name | Max group mean | Fold change | P-value | FDR p-value |
| --- | --- | --- | --- | --- |
| g_*Pseudomonas*, 646549 | 4,453.00 | 1.03 | 0.72 | 0.77 |
| g_*Pseudomonas*, 225284 | 3,853.00 | 3.19 | 0.00 | 0.00 |
| g_*Prevotella*, 851822 | 3,841.00 | −1.86 | 7.42E−14 | 1.84E−12 |
| g_*Streptococcus*, 2024840 | 3,453.00 | 1.32 | 7.80E−4 | 7.34E−3 |
| g_*Prevotella*, 4304901 | 2,596.00 | −48.68 | 0.00 | 0.00 |
| g_*Campylobacter*, 1616059 | 2,408.00 | 1.13 | 0.15 | 0.37 |
| g_*[Prevotella]*, 4324196 | 2,284.00 | −1.75 | 6.13E−11 | 1.31E−9 |
| g_*Streptococcus*, 516966 | 2,049.00 | −2.90 | 0.00 | 0.00 |

TABLE 1-continued

Details of genera level differences enriched in CLAD compared to non-CLAD

| Name | Max group mean | Fold change | P-value | FDR p-value |
| --- | --- | --- | --- | --- |
| g_Fusobacterium, 938948 | 1,809.00 | −2.36 | 0.00 | 0.00 |
| g_Haemophilus, 341460 | 1,785.00 | −3.99 | 0.00 | 0.00 |
| g_Neisseria, 4352493 | 1,714.00 | −18,207.59 | 8.08E−4 | 7.56E−3 |
| g_Leptotrichia, 2480553 | 1,504.00 | −15,976.96 | 9.49E−4 | 8.83E−3 |
| g_Porphyromonas, 4301737 | 1,125.00 | −2.95 | 0.00 | 0.00 |
| g_Fusobacterium, 4473295 | 1,119.00 | −2.08 | 3.00E−15 | 8.64E−14 |
| g_Granulicatella, 1696853 | 1,068.00 | 1.82 | 5.13E−10 | 1.00E−8 |
| g_Megasphaera, 4296242 | 1,043.00 | −2.00 | 1.21E−13 | 2.97E−12 |

Maximum group mean of at least 1000. Positive value fold change suggests increased CLAD while negative means reduced in CLAD group.

CLAD/non-CLAD microbial dysbiosis (MD) index was calculated and was noted to be −1.4, suggesting increased dysbiosis in the CLAD group. (Gevers D, Kugathasan S, Denson L A, et al. The treatment-naive microbiome in new-onset Crohn's disease. *Cell Host Microbe*. 2014; 15(3): 382-392).

Figure 3:
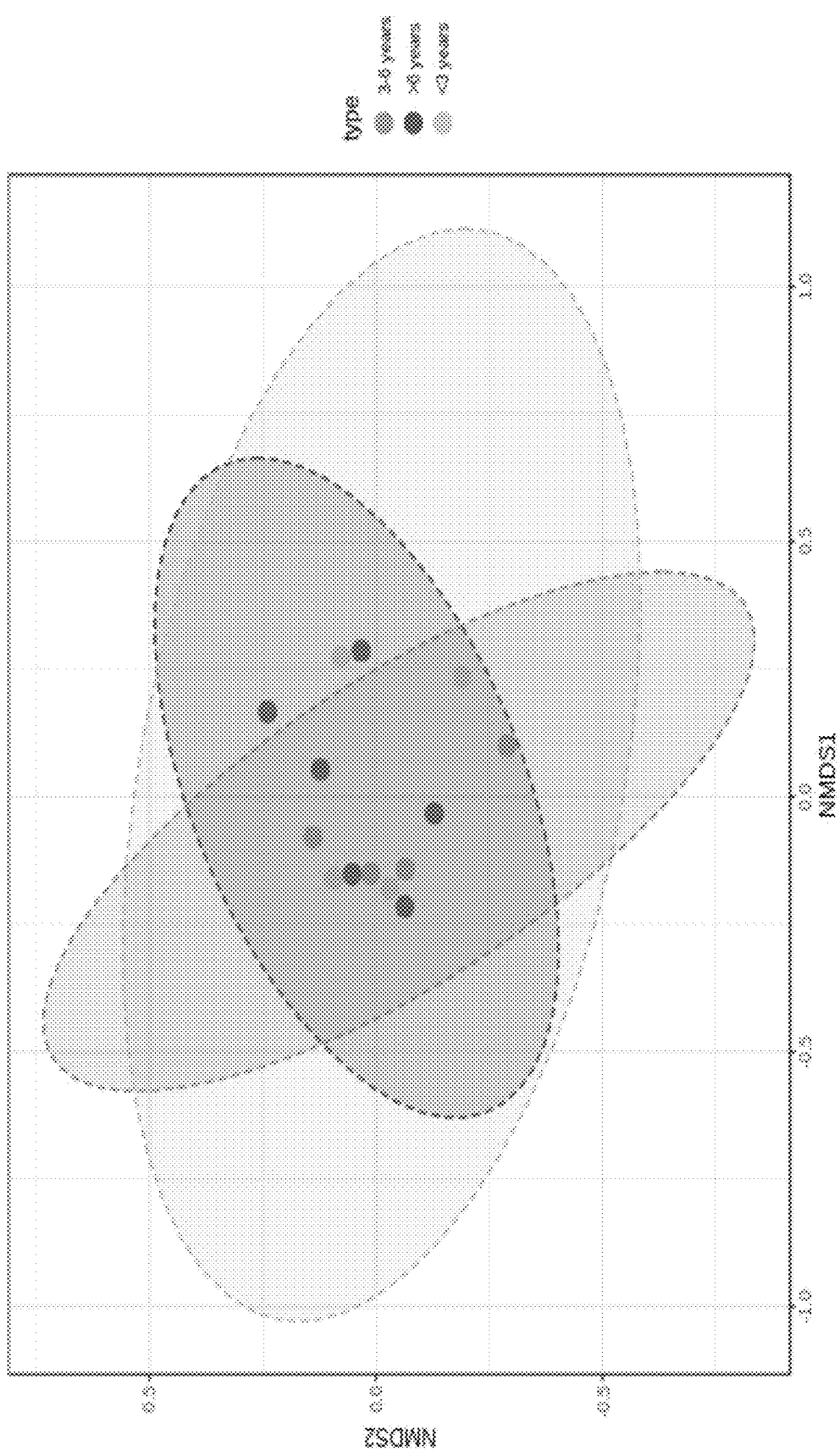
FIG. 3 is an image depicting nonmetric multi-dimensional scaling (NMDA) plot showing beta diversity between CLAD subject based on duration of transplantation. Bray-Curtis distance was utilized to plot beta-diversity and PERMANOVA for statistical analysis. CLAD subjects 3-6 years from transplant are shown in medium grey, >6 years from transplantation in dark grey and <3 years from transplantation in light grey. P value calculated via PERMANOVA analysis P=0.8. NMDS stress value of 0.11.
Figure 4:
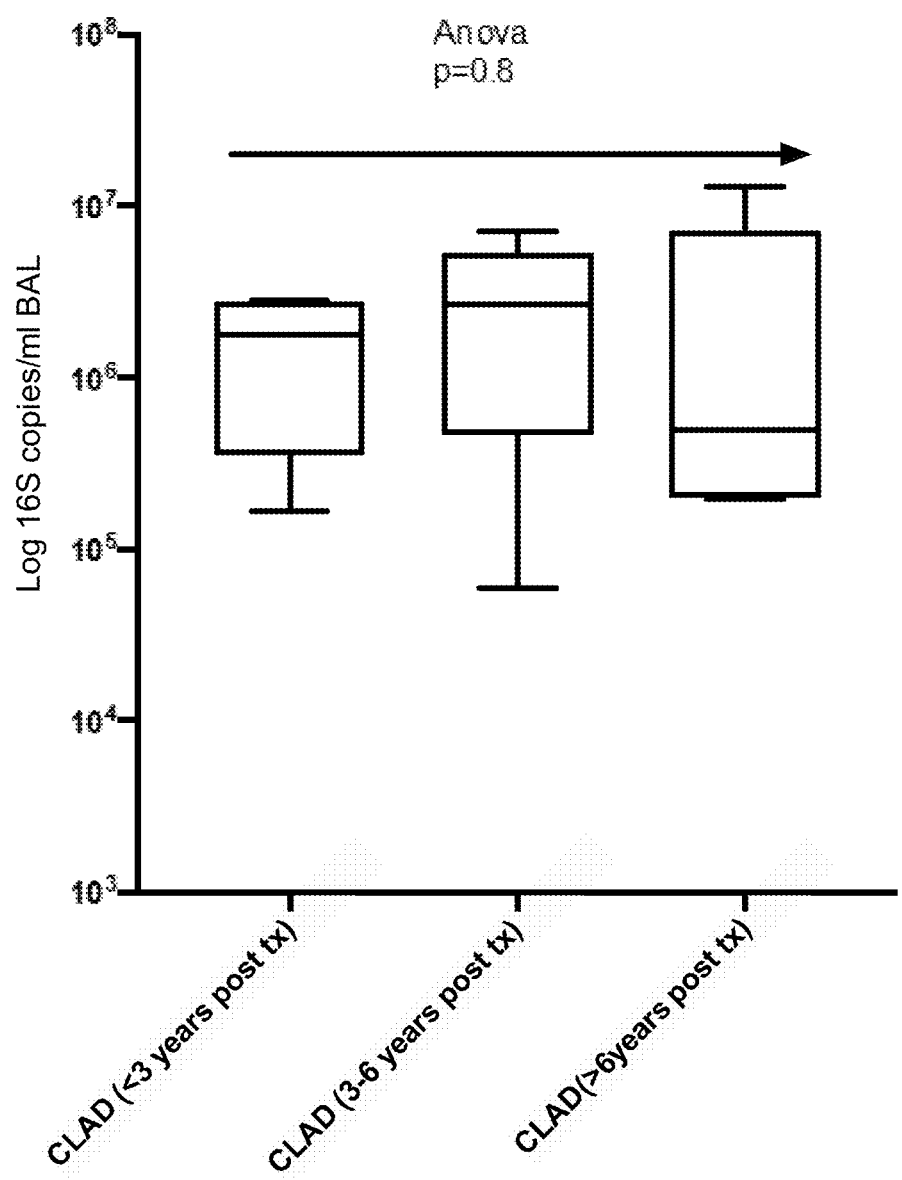
FIG. 4 is a graph depicting bacterial 16S gene copies/ml in BAL of CLAD subject based on duration of transplantation. Error bars showing mean±SEM, ****$P=0.8$ (ANOVA analysis).

Next, the inventors investigated whether time from transplantation influenced the taxonomic profile and/or bacterial biomass of the BAL specimens in CLAD subjects. Using BrayCurtis distance metric, we compared the beta diversity of CLAD subjects <3 years, 3-6 years and >6 years post-transplant. The NMDA plot showed overlap and no significant differences in beta diversity/taxonomic profile between the three groups (P=0.8, PERMANOVA) (FIG. 3). Likewise, the BAL bacterial biomass of CLAD subjects in the three groups based on time from transplantation were similar (FIG. 4).

Figure 5:
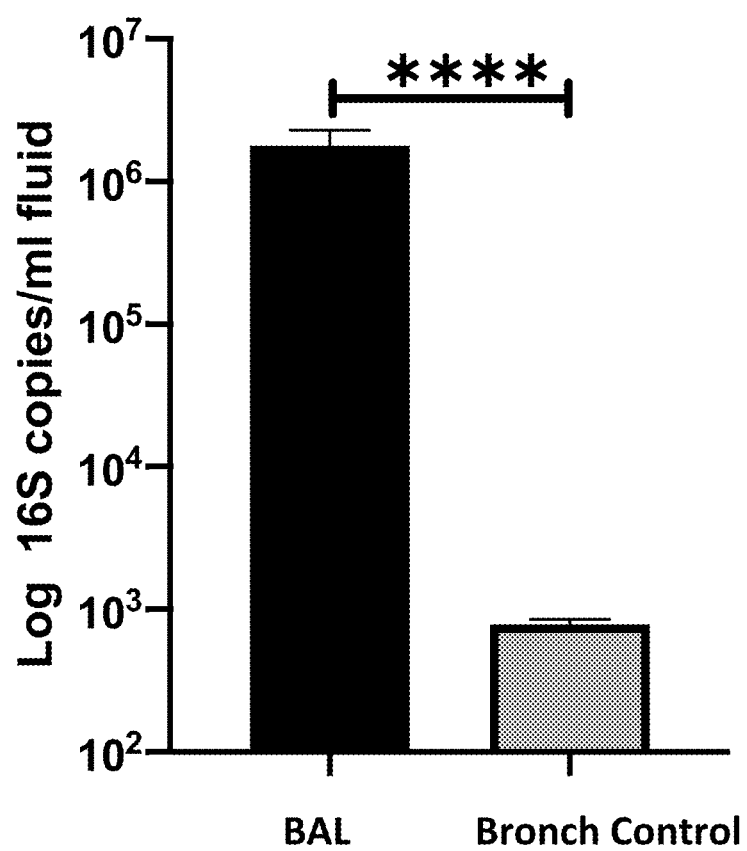
FIG. 5 is a graph depicting bacterial 16S gene copies/ml in BAL from lung transplant recipients and bronchoscope control samples. The Y-axis indicates 16S rRNA gene copy number by quantitative PCR, error bars showing mean±SEM, ****$P<0.0001$.
Figure 6:
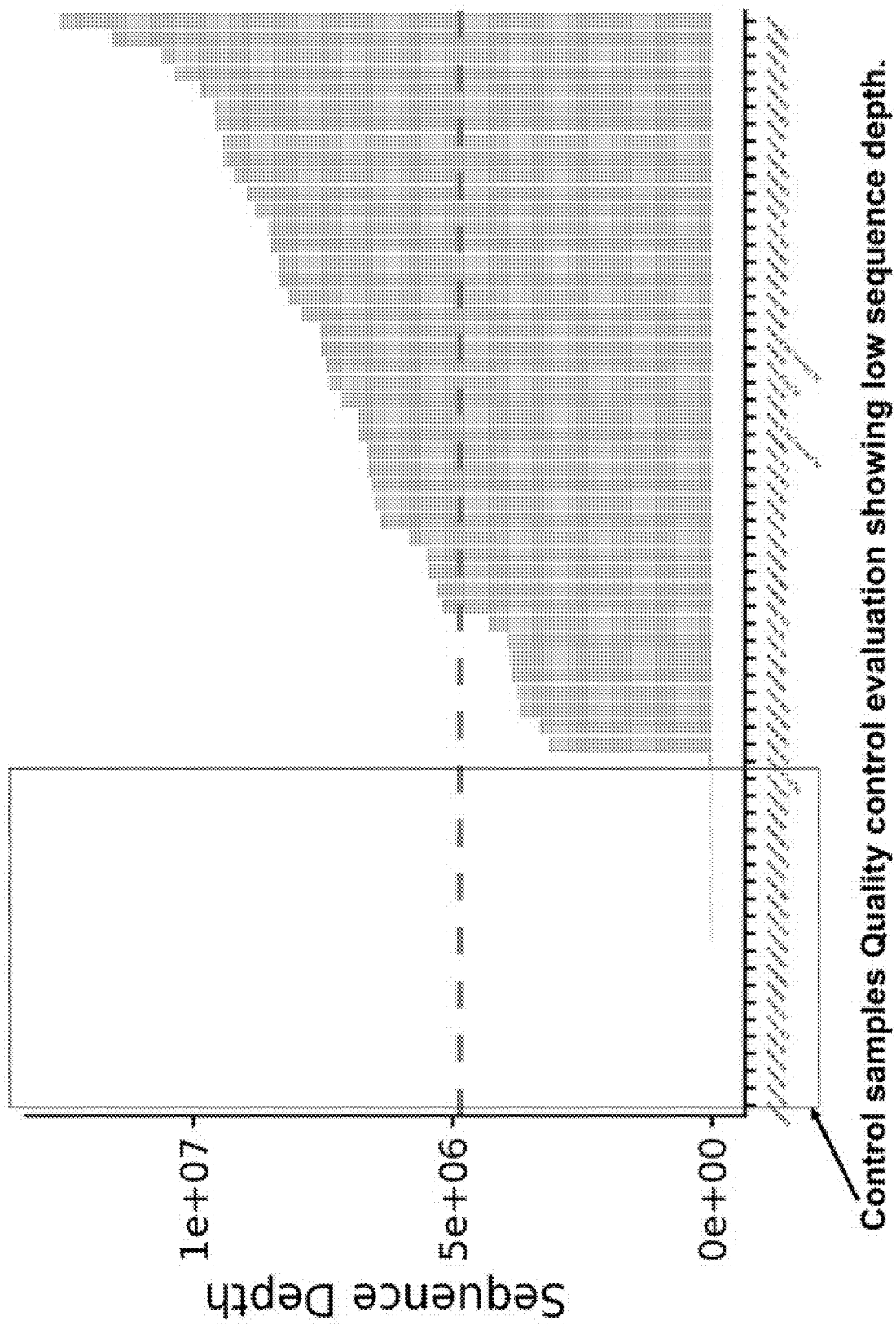
FIG. 6 is an image depicting quality control (QC) evaluation of sequenced control samples showing sequence depth in the Y-axis and samples on the X-axis. The marked box displays the sequence depth for the control samples.
Figure 7:
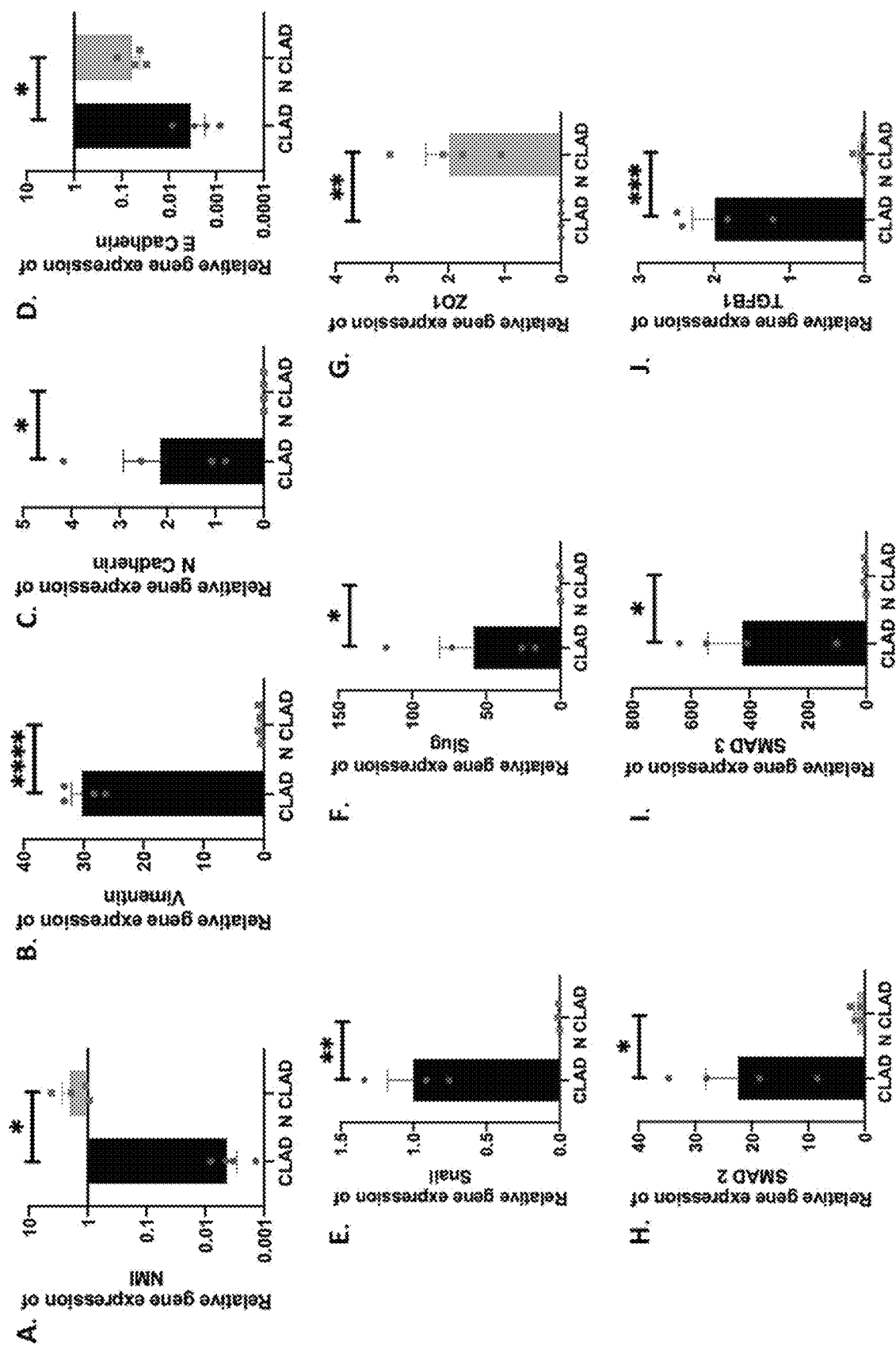
FIG. 7A-J are a series of graphs depicting gene expression of NMI and EMT markers in CLAD compared to non-CLAD. Relative expression of (A) NMI; EMT markers (vimentin, N-cadherin, and E-cadherin) (B) vimentin, (C) N-cadherin, and (D) E-cadherin; transcriptional factors (E) SNAIL and (F) SLUG; tight junction protein (G) ZO-1; and the TGF-β/SMAD pathway players (H) SMAD2, (I) SMAD3 and (J) TGF-01 in CLAD and non(N)-CLAD subjects are shown. All gene expression levels are normalized to GAPDH. Error bars represent mean±SEM. n=4.

To ensure quality control, we performed 16S qPCR and microbiome sequencing analysis on bronchoscope controls. The results revealed 16S gene copies in bronchoscope control significantly lower than that of the BAL sample (785 vs $1.77 \times 10^6$ per ml BAL, ****P<0.0001) (FIG. 5). The microbiome sequencing of the control samples did not reveal any reportable taxa due to extremely low sequencing depth suggesting extremely low biomass (FIG. 6).

Human CLAD Lungs are Associated with Downregulation of Gene N-Myc-Interactor and EMT Previous studies have proposed that EMT may contribute to the pathogenesis of CLAD. (Borthwick L A, Parker S M, Brougham K A, et al. Epithelial to mesenchymal transition (EMT) and airway remodelling after human lung transplantation. *Thorax*. 2009; 64(9):770-777; Renaud-Picard B, Valliere K, Toussaint J, et al. Epithelial-mesenchymal transition and membrane microparticles: Potential implications for bronchiolitis obliterans syndrome after lung transplantation. *Transpl Immunol*. 2020; 59:101273). The STAT regulatory gene NMI has been linked to EMT regulation and metastatic potential in several cancers. (Feng X, Xu X, Xiao X, et al. NMI inhibits cancer stem cell traits by downregulating hTERT in breast cancer. *Cell Death Dis*. 2017; 8(5):e2783). The inventors determined the expression of NMI and EMT in autopsy derived human CLAD tissues compared to non-CLAD lung transplant controls. Explant CLAD lung tissue showed a significantly reduced NMI gene expression, while the expressions of mesenchymal markers vimentin and N-cadherin was significantly increased, and that of epithelial marker E-cadherin reduced compared to non-CLAD lung tissues (FIG. 7A-D). Likewise, the gene expression of EMT transcriptional factors SLUG, TGF-β, SMAD 2/3 were increased, while that of tight junction protein ZO-1 was reduced in CLAD compared to non-CLAD controls (FIG. 7E-J). Similar gene expression profiles for NMI and EMT markers were noted when comparing freshly frozen CLAD explant lungs compared to healthy lung controls specimens (FIG. 8).

*Pseudomonas aeruginosa* Downregulates NMI and Induces EMT in Primary Bronchial Epithelial Cells Experiments were conducted to determine the role of the microbiome in the alteration of NMI expression and EMT response. The human CLAD cohort showed an increased abundance of the genus *Pseudomonas* in the BAL specimens. Thus, the inventors used PsA-PBEC co-culture (MOI 1:1 for 24 hours) as a model system to investigate the mucosal immune response. Exposure of PBECs to PsA resulted in downregulation of NMI. Moreover, the expression of mesenchymal markers vimentin and N-cadherin was increased and that of epithelial marker E-cadherin significantly reduced (FIGS. 9A and 9B).

Furthermore, protein expression of EMT transcription regulators SLUG/SNAIL was increased and that of the tight junction protein ZO-1 reduced in PsA-exposed PBECs (FIGS. 9C and 9D). The inventors' human microbiome studies revealed a significant increase in commensal bacteria *Prevotella melaninogenica* (PM) in the non-CLAD cohort. Exposure of PBECs to PM did not result in downregulation of NMI (FIG. 10). NMI is known to regulate EMT via the NF-κB or TGF-β/SMAD pathways. (Gonzalez D M, Medici D. Signaling mechanisms of the epithelial-mesenchymal transition. *Sci Signal*. 2014; 7(344):re8). To investigate the mechanistic pathway involved in PsA-induced EMT in PBECs, the inventors determined expression of key pathway mediators. The results showed upregulation of canonical TGFβ/SMAD pathways, while NF-κB expression was unchanged in PsA-exposed PBECs (FIG. 11). To further validate the mechanism, the inventors measured the protein expression of phosphorylated SMAD 2/3 complex that was found to be significantly upregulated in the PsA group.

NMI Regulates EMT in Primary Bronchial Epithelial Cells

NMI is a STAT interactor protein that has been found to regulate EMT in several cancers. (Devine D J, Rostas J W, Metge B J, et al. Loss of N-Myc interactor promotes epithelial-mesenchymal transition by activation of TGF-beta/SMAD signaling. *Oncogene*. 2014; 33(20):2620-2628). The role of NMI in the chronic lung diseases and CLAD pathobiology has not been delineated.

The inventors evaluated if NMI expression regulated EMT in PBECs and performed siRNA silencing and NMI overexpression in our PBEC model. Remarkably, NMI silencing resulted in increased expression of mesenchymal markers vimentin and N-cadherin, and reduced expression of E-cadherin, thus mirroring our results from PsA exposure.

Conversely, overexpression of NMI resulted in increase in E-cadherin and reduction in vimentin and N-cadherin expression (FIGS. 12A & B, FIG. 13).

Overexpression of NMI Mitigates PsA-Induced EMT Response in Primary Bronchial Epithelial Cells In order to determine whether NMI is a key mediator of PsA-induced EMT response in PBECs, the inventors performed NMI overexpression in PBECs followed by PsA-LPS exposure. First, NMI overexpression was confirmed in PBECs (FIG. 14). Exposure of PBECs to PsA-LPS showed a similar EMT response as with PsA exposure. NMI-overexpressing PBECs when exposed to PsA-LPS did not elicit an EMT response with insignificant changes in protein expression of mesenchymal markers vimentin and N-cadherin and epithelial marker E-cadherin suggesting that NMI upregulation mitigates the effect of PSA-LPS treatment on PBECs.

Materials and Methods

Subjects

Human subjects for the study were recruited from the adult lung transplant center at the University of South Florida/Tampa General Hospital between November 2017 to November 2019. Serial subjects undergoing bronchoscopy for CLAD suspicion were included in the study. Age-matched control non-CLAD transplant subjects were included. CLAD was adjudicated based on ISHLT guidelines. (Glanville A R, Verleden G M, Todd J L, et al. Chronic lung allograft dysfunction: Definition and update of restrictive allograft syndrome-A consensus report from the Pulmonary Council of the ISHLT. *The Journal of heart and lung transplantation: the official publication of the International Society for Heart Transplantation.* 2019; 38(5):483-492).

CLAD and non-CLAD explant lungs were procured from re-transplanted subjects or from general autopsy. Written consent was obtained for sample collection under an Institutional Review Board-approved protocol (University of South Florida IRB Pro #Pro00032158). Demographic details of the subjects and individual subject bronchoscopy and pulmonary function test details are presented in Table 2 & Table 3. Likewise, autopsy derived CLAD, autopsy derived non-CLAD, freshly collected CLAD and freshly collected healthy lung tissues were procured from re-transplant subjects or those who underwent autopsy/wedge biopsy. Demographic details of these subjects are detailed in Table 4.

TABLE 2

Demographic table of CLAD and non-CLAD subjects

|  | CLAD (n = 14) | Non-CLAD (n = 14) |
|---|---|---|
| Age-years (mean (SD)) | 64.7 (8.12) | 62.5 (5.74) |
| Gender (% male) | 92% | 86% |
| Pre-Transplant Diagnosis |  |  |
| IPF (%) | 86% | 43% |
| COPD (%) | 14% | 36% |
| CTD-ILD (%) |  | 7% |
| Other (%) |  |  |
| Chronic HP |  | 7% |
| COP |  | 7% |
| FEV1 (L) (Mean (SD)) | 2.11 (0.69) | 2.45 (0.64) |
| FVC (L) (Mean (SD)) | 3.4 (1.11) | 2.99 (0.87) |
| BAL Culture Positivity rate (%) | 28% | 7% |
| Years post-transplant (Mean (SD)) | 6.1(2.48) | 2.8 (2.43) |
| Grade of BOS-CLAD (%) |  |  |
| 0P | 22% |  |
| 1 | 42% |  |
| 2 | 22% |  |
| 3 | 14% |  |
| Immunosuppression (IS) |  |  |
| % on three drug IS (Tac, Pred, Myco/Aza/Siro) | 86% | 86% |
| % on two drug IS (Tac, Pred) | 14% | 14% |
| Prophylactic antibiotics |  |  |
| % on Bactrim | 100% | 100% |
| % on Azithromycin | 100% | 86% |

Abbreviations:
Tac—tacrolimus,
Pred—prednisone,
Myco—mycophenolate,
Aza—azathioprine,
Siro—sirolimus,
Chronic HP—Hypersensitivity Pneumonitis,
COP—cryptogenic organizing pneumonia

TABLE 3

Individual subject bronchoscopy and pulmonary function characteristics.

| Subject No | Bronchoscopy Indication | CLAD (Y/N) | BAL culture | FEV1/FVC (L) At BAL collection | FEV1/FVC (L) >3 months f/u after BAL | FEV1/FVC (L) Best post-transplant | CLAD grade at BAL collection | CLAD grade Follow-up (>3 months) |
|---|---|---|---|---|---|---|---|---|
| 1 | DLF | Y | *Penicillium* sps.(not treated) | 1.25/1.45 | 1.0/1.61 | 2.12/2.62 | 2 | 3 |
| 2 | DLF | Y | Negative | 1.76/3.85 | 1.20/3.02 | 3.49/4.49 | 2 | 3 |
| 3 | DLF | Y | Negative | 1.62/3.42 | 1.64/3.65 | 3.29/4.44 | 3 | 3 |
| 4 | DLF | Y | Negative | 2.77/5.96 | 2.51/5.87 | 4.15/6.26 | 1 | 2 |
| 5 | DLF | Y | *Klebsiella pneumoniae* | 2.26/2.73 | 1.69/2.04 | 3.16/3.98 | 1 | 2 |
| 6 | DLF | Y | *Klebsiella pneumoniae* | 1.28/2.73 | 0.83/2.19 | 3.16/4.01 | 3 | 3 |
| 7 | DLF | Y | *Hemophilus parainfluenzae* | 2.68/3.97 | 2.34/3.61 | 3.64/4.64 | 1 | 2 |
| 8 | DLF | Y | Negative | 3.02/4.46 | 2.85/4.20 | 3.78/4.74 | 1 | 1 |
| 9 | DLF | Y | Negative | 1.74/2.99 | 1.77/2.91 | 2.78/3.95 | 2 | 2 |
| 10 | DLF | Y | Negative | 2.62/2.97 | 2.12/2.58 | 3.0/3.41 | $0_P$ | 1 |
| 11 | DLF | Y | Negative | 2.71/3.91 | 1.89/3.26 | 3.27/3.95 | 1 | 2 |

TABLE 3-continued

Individual subject bronchoscopy and pulmonary function characteristics.

| Subject No | Bronchoscopy Indication | CLAD (Y/N) | BAL culture | FEV1/FVC (L) At BAL collection | FEV1/FVC (L) >3 months f/u after BAL | FEV1/FVC (L) Best post-transplant | CLAD grade at BAL collection | CLAD grade Follow-up (>3 months) |
|---|---|---|---|---|---|---|---|---|
| 12 | DLF | Y | Negative | 2.17/2.91 | 0.76/2.11 | 2.58/3.2 | $0_P$ | 3 |
| 13 | DLF | Y | Negative | 1.34/2.39 | 1.30/2.38 | 1.76/2.64 | 1 | 1 |
| 14 | DLF | Y | Negative | 3.34/4.45 | 3.14/4.28 | 3.96/4.91 | $0_P$ | 1 |
| 15 | DLF | N | Negative | 1.74/2.30 | 1.81/2.40 | 1.99/2.97 | NA | NA |
| 16 | Surveillance | N | Negative | 3.43/3.77 | 3.7/4.26 | 3.7/4.26 | NA | NA |
| 17 | Surveillance | N | Negative | 2.78/3.57 | 3.47/4.3 | 3.47/4.3 | NA | NA |
| 18 | Surveillance | N | Negative | 2.66/2.76 | 2.68/3.20 | 2.83/3.45 | NA | NA |
| 19 | Surveillance | N | Negative | 2.88/3.31 | 2.86/3.11 | 3.07/3.45 | NA | NA |
| 20 | Surveillance | N | Negative | 2.11/2.50 | 2.17/2.24 | 2.22/2.82 | NA | NA |
| 21 | Surveillance | N | Negative | 2.50/3.12 | 3.01/3.69 | 3.01/3.69 | NA | NA |
| 22 | Surveillance | N | Negative | 2.53/3.25 | 2.84/3.67 | 3.09/3.99 | NA | NA |
| 23 | DLF | N | Hemophilus parainfluenzae | 3.58/5.06 | 4.03/5.44 | 4.03/5.44 | NA | NA |
| 24 | Surveillance | N | Negative | 2.36/2.91 | 2.75/3.44 | 2.75/3.44 | NA | NA |
| 25 | Surveillance | N | Negative | 1.74/1.95 | 2.30/3.31 | 2.30/3.31 | NA | NA |
| 26 | Surveillance | N | Negative | 2.29/3.64 | 2.27/3.56 | 2.29/3.64 | NA | NA |
| 27 | Surveillance | N | Negative | 1.94/2.87 | 2.64/3.73 | 2.73/4.02 | NA | NA |
| 28 | Surveillance | N | Negative | 1.93/2.29 | 2.5/2.98 | 2.5/2.98 | NA | NA |

DLF = drop in lung function

TABLE 4

Demographic details of subjects from which explant/autopsy tissues analyzed

| Age | Gender | Pre Tx-diagnosis | CLAD | Time from Transplant when specimen collected |
|---|---|---|---|---|
| 57 | M | IPF | Y | 61 months |
| 57 | F | A1AT | Y | 35 months |
| 62 | M | IPF | Y | 84 months |
| 33 | F | CF | Y | 80 months |
| 60 | M | COPD | N | 37 months |
| 67 | M | IPF | N | 27 months |
| 68 | M | COPD | N | 14 months |
| 50 | M | IPF | N | 30 months |

Autopsy lungs of CLAD subjects (re-transplanted patients) and non-CLAD transplant recipients (who died of non-allograft issues) were processed and used for qPCR and Western blot analyses using published methods described in Smirnova et al., herein incorporated by reference into this disclosure (Smirnova N F, Conlon T M, Morrone C, et al. Inhibition of B cell-dependent lymphoid follicle formation prevents lymphocytic bronchiolitis after lung transplantation. *JCI Insight.* 2019; 4(3):e123971).

In addition, freshly acquired CLAD lung explant specimens and healthy human lung specimens were also collected and processed as above. For BAL collection a total of 120 ml of saline (4 aliquots of 30 cc) was instilled in either the right middle lobe or lingula per physician preference. Remnant BAL fluid was collected from the last aliquot fraction.

The lung microbiome has a relatively lower biomass compared to the GI microbiome. (Pruitt H C, Metge B J, Weeks S E, et al. Conditional knockout of N-Myc and STAT interactor disrupts normal mammary development and enhances metastatic ability of mammary tumors. *Oncogene.* 2018; 37(12):1610-1623; Wang J, Zou K, Feng X, et al. Downregulation of NMI promotes tumor growth and predicts poor prognosis in human lung adenocarcinomas. *Mol Cancer.* 2017; 16(1):158). Interpretation of results from low biomass without appropriate controls can be erroneous. Hence, bronchoscope control samples were collected from each bronchoscope used prior to the procedure (25 ml of sterile saline flushed via the bronchoscope and collected). BAL fluid samples were processed using the inventors published methodology. Briefly, BAL fluid samples were centrifuged at 1,000 rpm for 5 minutes to separate the eukaryotic cellular fraction. The supernatants were centrifuged again at 15,000 rpm for 10 minutes to pellet the bacterial component. Similarly, control (C) samples from each bronchoscope used were collected and centrifuged at 15,000 rpm for 10 minutes to pellet the bacterial component. All bacterial pellets were then stored at −80° C.

Human Sample Sequencing 16S microbiome sequencing (Illumina MiSeq platform) and 16S qPCR were performed using established protocol as described in Sharma et al. 2017 and Sharma et al. 2020, herein incorporated by reference into this disclosure. (Sharma N S, Wille K M, Athira S, et al. Distal airway microbiome is associated with immunoregulatory myeloid cell responses in lung transplant recipients. *The Journal of heart and lung transplantation: the official publication of the International Society for Heart Transplantation.* 2017; 37(2):P206; Sharma N S, Vestal G, Wille K, et al. Differences in airway microbiome and metabolome of single lung transplant recipients. *Respir Res.* 2020; 21(1):104)).

Isolation of Microbial DNA and Creation of 16S V4 Amplicon Library

Microbial genomic DNA was isolated using the Fecal DNA isolation kit (Zymo Research, Irvine, CA) following the manufacturer's instructions. Once the sample DNA was prepared, PCR was used with unique bar-coded primers to amplify the V3-V4 region of the 16S rRNA gene to create an "amplicon library" from individual samples as described in Kozich et al. and Kumar et al., herein incorporated by reference into this disclosure (Kozich, J. J., Westcott, S. L., Baxter, N. T., Highlander, S. K., and Schloss, P. D. Development of a dual-index sequencing strategy and curation pipeline for analyzing amplicon sequence data on the MiSeq Illumina sequencing platform. *Applied and environmental microbiology.* 2013; 79:5112-5120; Kumar, R., Eipers, P., Little, R. B., Crowley, M., Crossman, D. K., Lefkowitz, E.

J. and Morrow, C. D. 2014. Getting Started with Microbiome Analysis: Sample Acquisition to Bioinformatics. *Current Protocols in Human Genetics*. 18.8.1-18.8.28, July 2014 Published online July 2014).

The primers were synthesized at 50 nmol scale with desalting purification (Eurofins-mwg-operon, Huntsville, AL). The primers were diluted with 10 mM Tris pH 8.0 to 100 µM, then diluted 10-fold in water to 10 µM for use in PCR reactions. Primers used were as follows: 5' Primer 5'-AATGATACGGCGACCACCGAGATCTACAC-TATGGTAATTGTGTGCCAGCMG CCGCGGTAA-3' (SEQ ID NO: 1) and 3' Primer: 5'-CAAGAGAAGACGG-CATACGAGATNNNNNNAGTCAGTCAGCCGGAC-TACHV GGGTWTCTAAT-3' (SEQ ID NO: 2). Following PCR, the entire PCR reaction was electrophoresed on a 1.0% agarose/Tris-borate-EDTA gel. The PCR product (approximately 380 base pair predicted product size) was visualized by UV illumination. The band was excised and purified from the agarose using QIAquick Gel Extraction Kit according to manufacturer's instructions. (Qiagen, Valencia, CA).

DNA Sequencing

The PCR products were sequenced using NextGen sequencing Illumina MiSeq platform as described in Kozich et al. and Kumar et al., herein incorporated by reference into this disclosure (Kozich, J. J., Westcott, S. L., Baxter, N. T., Highlander, S. K., and Schloss, P. D. Development of a dual-index sequencing strategy and curation pipeline for analyzing amplicon sequence data on the MiSeq Illumina sequencing platform. *Applied and environmental microbiology*. 2013; 79:5112-5120; Kumar, R., Eipers, P., Little, R. B., Crowley, M., Crossman, D. K., Lefkowitz, E. J. and Morrow, C. D. 2014. Getting Started with Microbiome Analysis: Sample Acquisition to Bioinformatics. *Current Protocols in Human Genetics*. 18.8.1-18.8.28, July 2014 Published online July 2014). The MiSeq is a single flowcell, single lane instrument that can generate approximately 9 Gb of sequence data from a paired end 250 bp run (Caparoso et. al. 2012. Ultra-high-throughput microbial community analysis on the Illumina HiSeq and MiSeq platforms. *The ISME journal* 6:1621-1624). The paired 250 base pair end kits from Illumina were used for the V4 region in the microbiome analysis. The samples were first quantitated using Pico Green, adjusted to a concentration of 4 nM and then used for sequencing on the Illumina MiSeq per Kumar et. al. 2014.

Fastq conversion of the raw data files was performed following de-multiplexing. Quality control of the fastq files was performed then subject to quality assessment and filtering using the FASTX toolkit (FASTX). The remainder of the steps was performed with the CLC genomics workbench using Greengenes reference database.

Bioinformatics

The sequence data covered the 16S rRNA V4 region with a PCR product length of ~255 bases and 250 base paired-end reads. Since the overlap between fragments was approximately 245 bases, the information from both ends of the paired reads was merged to generate a single high quality read. Read pairs with an overlap of less than 50 bases or with too many mismatches (>20) in the overlapping region were discarded. Chimeric sequences were also filtered. Overall read quality was assessed before and after filtering.

The QIIME data analysis package was used for subsequent 16S rRNA data analysis (Caparoso et al., 2012. Ultra-high-throughput microbial community analysis on the Illumina HiSeq and MiSeq platforms. *The ISME journal* 6:1621-1624). Sequences were grouped into operational taxonomic units (OTUs) using the clustering program UCLUST at a similarity threshold of 0.97% (Edgar, R. C. 2010. Search and clustering orders of magnitude faster than BLAST. Bioinformatics (Oxford, England) 26:2460-2461). The Ribosomal Database Program (RDP) classifier was used to make taxonomic assignments (to the species level) for all OTUs at confidence threshold of 60% (0.6) (Wang et al., 2007. Naive Bayesian classifier for rapid assignment of rRNA sequences into the new bacterial taxonomy. *Applied and environmental microbiology* 73:5261-5267). The RDP classifier was trained using the Greengenes (v13_8) 16S rRNA database (McDonald, et al., 2012. An improved Greengenes taxonomy with explicit ranks for ecological and evolutionary analyses of bacteria and archaea. *The ISME journal* 6:610-618). The resulting OTU table included all OTUs, their taxonomic identification, and abundance information. OTUs whose average abundance was less than 0.0005% were filtered out. OTUs were then grouped together to summarize taxon abundance at different hierarchical levels of classification (e.g., phylum, class, order, family, genus, and species). These taxonomy tables were also used to generate bar charts of taxon abundance. Multiple sequence alignment of OTUs was performed with PyNAST (Caporaso, et al., 2010a. PyNAST: a flexible tool for aligning sequences to a template alignment. *Bioinformatics (Oxford, England)* 26:266-267). Alpha diversity (within sample diversity) was calculated using a variety of diversity metrics including Shannon's, Chao1, and Simpson, as implemented in CLC workbench. Beta diversity (between sample diversity) among different samples was measured using Bray Curtis metrics (Lozupone et al. 2006. UniFrac—An online tool for comparing microbial community diversity in a phylogenetic context. *BMC bioinformatics* 7:371). Principal coordinates analysis (PCoA) was performed CLC to visualize the dissimilarity matrix (beta-diversity) between all the samples, such that samples that are more similar are closer in space than samples that are more divergent. 3D PCoA plots were generated using EMPEROR (Vizquez-Baeza Y et al., Vizquez-Baeza Y, Pirrung M, Gonzalez A, Knight R. 2013, EMPeror: a tool for visualizing high-throughput microbial community data. *GigaScience* 2013; 2:16). NMDS plot was generated using microbiomeanalyst.

Bacterial Quantification Via 16S qPCR

To generate quantification curves, purified DNA from *Pseudomonas aeruginosa* was quantified using a Qubit Fluorometric estimation (Thermo Fisher Scientific). This DNA was subsequently diluted serially by copy number (calculated by molecular weight) and amplified using the 16S rRNA qRT-PCR assay.

A standard curve of Ct value vs copy number was plotted using the serially diluted samples using RT PCR and finally the bacterial load in the BAL fluid were extrapolated from the curve.

16S Primers used were 5'-GCAGGCCTAACA-CATGCAAGTC-3' (63F) (SEQ ID NO: 3) and 5'-CTGCTGCCTCCCGTAGGAGT-3' (355R) (SEQ ID NO: 4). The cycling protocol was 1 cycle at 95° C. for 5 minutes, 40 cycles at 95° C. for 15 seconds and 60° C. for 1 minute, 1 cycle at 4° C. for 5 minutes, and 1 cycle at 90° C. for 5 minutes all at a ramp rate of 2° C./second. The BioRad C1000 Touch Thermal Cycler was used for PCR cycling. Three replicates were used per sample. Negative control specimens were used and were run alongside lung specimens. The bacterial burden in bronchoalveolar lavage specimens as well as the controls were reported as total bacterial 16S gene copies per mL of lavage fluid.

Cell Culture and Reagents

Normal human primary bronchial/tracheal epithelial cells (PBEC) (ATCC PCS-300-010) were used. The cells were maintained in Airway Epithelial Cell Basal (AECB) Medium supplemented with growth kit components recommended and procured from ATCC at 37° C. in a humidified 5% $CO_2$ incubator. The maintenance and propagation were done as per ATCC recommendations.

siRNA Knockdown and NMI Overexpression Experiments

A mixture of three siRNAs specific to NMI were procured from IDT (Coraville, IA). Cells were plated into a 35 mm 6-well plate and allowed to reach a confluency of approximately 80%. Transfections were performed in opti-MEM media (ThermoFisher Scientific) using Lipofectamine RNAi max (Life Technologies USA) according to manufacturer's instructions. NMI (Myc-DDK-tagged)-Human N-myc (and STAT) interactor (NMI) plasmid was procured from ORIGENE technologies (Rockville, USA) and transfected into Normal human Primary bronchial/tracheal epithelial cells using Lipofectamine 3000 (Life Technologies USA) according to manufacturer's instructions.

Pseudomonas Co-Cultivation Experiments

Pseudomonas aeruginosa strain PAO1 (ATCC BAA-47) was grown in tryptic soy broth (BD Bacto, ThermoFisher) and incubated at 37° C. in a rotary shaker for 16 hours. Bacteria density was measured by optical density ($OD_{260}$) and microscopic counting. For bacteria-PBEC co-cultivation experiments, epithelial cells were grown in 24-well plates in 1 ml or 6-well plates in 3 ml of AECB medium per well until cells reached 70-80% confluency. Subsequently, bacteria were added at a bacteria-PBEC ratio of 1:1 in AECB medium without antibiotics and plates were incubated overnight for 16 hours at 37° C. in the $CO_2$ incubator followed by isolation of RNA for quantitative RT-PCR or protein for Western blot analysis.

RNA Isolation and Real Time PCR

Lung tissues that had been stored in −80° C. were transferred to liquid nitrogen and pulverized. Subsequently RNA extraction from them was done with Qiagen RNA mini kit. FFPE samples were de-paraffinized and total RNA was extracted from them using Qiagen RNA FFPE kit following manufacturer's instructions. Total RNA in both cases was converted to cDNA using iScript kit (BioRad). All RT PCR experiments were performed on Quant Studio 3 (Applied Biosystems) using SYBR green mix (Applied Biosystems) and Ct values were obtained. The fold change values in expression were determined by Livak method.

Western Blot Analysis

Cells were harvested and lysed in RIPA buffer (EMD Millipore, USA) supplemented with protease and phosphatase inhibitor cocktail (Sigma-Aldrich, Catalog no. P8340 and ThermoFisher Scientific, Catalog no. 78420). The lysates were centrifuged at 10,000 rpm at 4° C. and the supernatants (10-20 μg) were separated on 4-20% precast polyacrylamide gels (BioRad, USA). Membranes were incubated in primary antibodies and detected with their Horse-Radish Peroxidase labelled conjugates (Cell signaling, SantaCruz, and ThermoFisher, USA). Antibody conjugates were visualized using, Kwik Quant Western Blot Detection kit (Kidle Biosciences, LLC, USA). Densitometry calculations were performed by ImageJ Software (NIH). All results were normalized to GAPDH.

GAPDH and NMI have extremely close molecular weights. To distinguish between the two proteins, we ran replicate gels with the same specimen. GAPDH and NMI were probed in these separate replicate gels (Similar sample was run in corresponding lanes). All results were normalized to GAPDH. The NMI clone has human NMI cloned into pCMV6-Entry vector with a MYCDDK tag at its C terminal for the purpose of probing the exogenous protein.

The NMI overexpression clone was procured from Origene (CAT #: RC201543). The said clone has human NMI cloned into pCMV6-Entry vector with a MYCDDK tag at its C terminal for the purpose of probing the exogenous protein. The overhang adds an additional 2.8 kD to the exogenous NMI (thus making its molecular mass 38.8 kD) and hence the two bands are seen in the NMI blot in overexpression lanes of FIG. 12A. The lower one being the endogenous NMI and the upper one being the exogenous one.

Likewise, E-cadherin contains a number of cleavage sites which may yield a complex fragmentation pattern in Western Blotting. E-Cad full-length (E-Cad-FL, 135 kDa) and two minor fragments at 85 kDa (E-Cad-85) and 23 kDa (E-Cad-23) have been detected by western blotting in different biological/disease contexts. The Full-length protein is 135 kDa the major E cadherin fragment involved in mediating cell to cell adhesion. We found two of these fragments in our experiments. The major one at 135 kD and a minor one (85 kD) which runs between 75 and 100 kDa markers (FIG. 12). The relative proportion of the lower band (85 kD) is very low and is mainly picked in normal conditions or in conditions where NMI was overexpressed and EMT reversed (FIG. 13).

Statistical Analysis

To compare β-diversities between CLAD and non-CLAD airway microbiome, the Bray-Curtis distance metric was calculated of log transformed data between all samples and then plotted separately using non-metric multi-dimensional scaling (NMDA) plot. Significant differences in community membership identified were confirmed by using PERMANOVA (permutational multivariate analysis of variance). Differential abundance using non-parametric measures to identify features at the phylum and/or genus levels that were distinctive between CLAD and non-CLAD airway microbiome and false discovery rate (Benjamini-Hochberg) calculated with cutoff of 0.05. Differentially abundant operational taxonomic units (OTUs) were used to calculate the microbial dysbiosis index (MD-index) CLC Genomics workbench and microbiomeanalyst software's were used to analyze and plot the microbiome data. Greengenes database (97%) was used for taxonomic classification. For statistical testing, the inventors first determined normality for each data set using Shapiro-Wilk test and then performed the appropriate statistical testing. Details of individual tests used are provided in the figure legends. GraphPad Prism version 8.0 was used to analyze and plot the in vitro data. Illustration for FIG. 15 was done using BioRender Illustrator.

Conclusion

CLAD is associated with reduced bacterial diversity, increased bacterial biomass, Gammaproteobacteria dominant airway microbiome and EMT. PsA induces EMT in human bronchial epithelial cells. NMI is a critical regulator of PsA-induced airway EMT.

The inventors show a distinct microbiome in CLAD subjects with a higher abundance of Proteobacteria and a lower Bacteriodetes level as compared with those without CLAD. The inventors also describe a new mechanism illuminating the role of the lung microbiome in regulating EMT and its potential role in the pathogenesis of CLAD. Future longitudinal studies need to be conducted to better inform the alterations of the lung microbiome that lead to the onset and progression of CLAD. Likewise, these studies can also shed light on the cross talk between the lung microbiome and NMI modulation that may contribute to CLAD pathogenesis.

Example 2—Biomarker for Predicting Development of EMT and Chronic Lung Disease (Prophetic)

A 55-year-old male patient undergoes a right lung transplant. After transplantation, the patient presents with difficulty expelling air. A sample from the transplanted lung is obtained from the patient and the expression level of NMI is measured. This result is compared to a control sample. The expression level of the patient sample is decreased as compared to the control sample. This is indicative of a diagnosis of a chronic lung disease such as CLAD. The patient is administered at least once a therapeutically effective amount of a therapeutic agent used to treat a chronic lung disease such as CLAD. After a period of time, the patient exhibits improvement in airflow when expelling air.

A 58-year-old female patient undergoes a left lung transplant. After transplantation, the patient has routine follow-up check-ups every 6 months during which a sample from the transplanted lung is obtained and the expression level of NMI is measured. During the first two check-ups, NMI expression levels are normal as compared to the control sample. At the third check-up after 1.5 years post-transplantation, the NMI expression level of the patient sample is now decreased as compared to the control sample. This is indicative of a diagnosis of the beginning of development of chronic lung disease such as CLAD, even before other symptoms of CLAD have developed. The patient is administered at least once a therapeutically effective amount of a therapeutic agent used to treat a chronic lung disease such as CLAD. After a period of time, the patient has normal NMI expression levels again. This early detection of onset of CLAD has helped this patient to prevent the development of more severe CLAD and rejection of her lung transplant.

Example 3—Use as Biomarker to Determine Treatment Efficacy (Prophetic)

A 65-year-old male patient presents with airway restriction after a right lung transplant. A sample from the transplanted lung is obtained from the patient and the expression level of NMI is measured. This result is compared to a control sample. The expression level of the patient sample is decreased as compared to the control sample. The patient is diagnosed with CLAD.

The patient is administered a therapeutically effective amount of a therapeutic agent used to treat CLAD. After a period of time, a second sample from the transplanted lung is obtained from the patient and the expression level of NMI of this second sample is measured and compared to the first sample. The expression level of the second sample exhibits an increased expression level of NMI as compared to the expression level of the first sample which is indicative of the therapeutic agent being efficacious.

Example 4—Drug Target to Augment NMI (Prophetic)

A 46-year-old male patient presents with airway restriction after a left lung transplant. A sample from the transplanted lung is obtained from the patient and the expression level of NMI is measured. The level of NMI in the sample taken from the patient is compared to a control sample. It is found that the patient sample exhibits a lower expression level as compared to the control sample and a diagnosis of CLAD is confirmed.

A therapeutically effective amount of an NMI amplifying drug is administered at least once to the patient to increase expression of NMI. After a period of time, improvement in airflow is exhibited in the patient.

Example 5—Therapeutic and Method for Treating CLAD (Prophetic)

A 53-year-old female patient presents with restricted airway flow after left lung transplantation. A sample is taken from the patient and the expression level of NMI is measured and compared to that of a control sample. The patient sample is determined to have a decreased expression level of NMI as compared to the control sample. The patient is diagnosed with a chronic lung disease, such as CLAD, characterized by decreased NMI.

A therapeutic agent is administered at least once intranasally. The therapeutic agent is in the form of a composition of NMI protein-coated nanoparticles in a pharmaceutically acceptable carrier. The inhaled composition delivers the nanoparticles to the lungs to increase NMI. After a period of time, improvement in airway flow is exhibited.

Example 6—Gene Therapy for Treating CLAD (Prophetic)

A 60-year-old male patient presents with restricted airway flow after left lung transplantation. A sample is taken from the patient and the expression level of NMI is measured and compared to that of a control sample. The patient sample is determined to have a decreased expression level of NMI as compared to the control sample. The patient is diagnosed with a chronic lung disease characterized by decreased NMI. A therapeutically effective amount of a therapeutic agent is administered at least once. The therapeutic agent is in the form of a nanoparticle composition comprising nanoparticles coated with NMI gene expression vector. Improvement in airway flow is exhibited after a period of time.

An NMI expression vector is formed from cDNA cloned from a *Homo sapiens* NMI gene. The NMI gene is fused to a gene encoding a secretion signaling peptide and the construct inserted into an expression vector under a promotor. The NMI vector is transformed in *E. coli* and then expanded in broth containing ampicillin to select for the vector. The vector is then collected and coated onto nanoparticles for delivery to the patient.

Example 7—Method of Reducing Risk of CLAD (Prophetic)

A 50-year-old male patient undergoes a right lung transplant. Before and/or after the transplant, the patient is administered a therapeutically effective amount of an antibiotic targeted to genus Proteobacteria, specifically targeted to *Pseudomonas aeruginosa* to increase the expression level of N-myc-interactor (NMI) in the patient. The patient does not develop symptoms of CLAD.

A 66-year-old male patient undergoes a left lung transplant. After the transplant, the patient is intranasally administered a therapeutically effective amount of a composition of nanoparticles comprised of NMI recombinant proteins in a pharmaceutically acceptable carrier to increase the expression level of N-myc-interactor (NMI) in the patient. The patient does not develop symptoms of CLAD.

A 70-year-old female patient undergoes a left lung transplant. After the transplant, the patient is administered a therapeutically effective amount of a composition of nanoparticles coated with the expression vector encoding the NMI gene and a pharmaceutically acceptable carrier to increase the expression level of N-myc-interactor (NMI) in the patient. The patient does not develop symptoms of CLAD.

A sample is optionally taken from each of the foregoing patients of Example 7 and NMI is measured and compared to a control and/or a bacterial culture is taken and compared to a control prior to administration of the therapeutic agent to establish a baseline. Second samples/cultures may be collected at a time period after administration of the therapeutic agent and the results compared to the first samples/cultures and corresponding controls to determine efficacy of prophylactic treatment.

Example 8—Method of Determining Pathogenesis of CLAD (Prophetic)

A 56-year-old female patient undergoes a right lung transplant and suffers from restricted airflow after the operation. A sample from the transplanted lung is obtained from the patient and the expression level of NMI is measured. This result is compared to a control sample. The expression level of the patient sample is decreased as compared to the control sample.

The sample is also cultured to determine the lung microbiome. The culture results exhibit an overabundance of Proteobacteria, specifically *Pseudomonas aeruginosa* as compared to a control. The decrease in NMI and the increase in *Pseudomonas aeruginosa* indicate pathogenesis of CLAD in the patient.

The patient is administered at least once a therapeutically effective amount of a therapeutic agent used to treat CLAD by reducing the amount of bacteria and/or by increasing the amount of NMI.

At a time period after administration of the therapeutic agent, a second sample is obtained from the patient and the expression level of NMI in the second sample is measured. The result is compared to the result from the first sample from the patient. An increase in NMI is observed. The expression level of the second sample is also compared to the control. The expression level of NMI from the second sample is observed as being similar to the control. In addition, the lung microbiome is also cultured a second time with the results being compared to the first culture as well as the control. The lung microbiome is found to have decreased Proteobacteria, specifically *Pseudomonas aeruginosa* as compared to the first culture with the results being similar to the control. The results of increasing NMI expression levels and decreasing Proteobacteria, specifically *Pseudomonas aeruginosa* indicates efficacy of the treatment and a favorable prognosis.

The disclosures of all publications cited above are expressly incorporated herein by reference, each in its entirety, to the same extent as if each were incorporated by reference individually.

It is also to be understood that the following claims are intended to cover all of the generic and specific features of the invention herein described, and all statements of the scope of the invention which, as a matter of language, might be said to fall there between. Now that the invention has been described,

---

What is claimed is:

1. A method of predicting and treating development of chronic lung allograft dysfunction (CLAD) in a patient in need thereof comprising:
   obtaining a sample from the patient;
   obtaining an expression level of N-myc-interactor (NMI) protein or gene in the sample;
   comparing the expression level of the NMI protein or gene in the sample to a control;
   wherein decreased expression of NMI protein or gene as compared to the control indicates the development of CLAD; and
   administering to the patient a therapeutically effective amount of a therapeutic agent selected from the group consisting of antibiotics, neomacrolides, montelukast, pirfenidone, nintedanib, alemtuzamab, immunosuppressants, beneficial bacteria, and an NMI modulator composition if development of CLAD is indicated.

2. The method of claim 1, further comprising determining or having determined a microbiome signature of the sample wherein a higher level of phylum Proteobacteria and a lower level of phylum Bacteriodetes in the sample as compared to a control is indicative of increased risk of the patient developing CLAD.

3. The method of claim 1, wherein the therapeutic agent is the NMI modulator composition wherein the NMI modulator composition comprises nanoparticles coated with NMI recombinant protein and a pharmaceutically acceptable carrier.

4. The method of claim 1, wherein the therapeutic agent is the NMI modulator composition wherein the NMI modulator composition comprises nanoparticles coated with NMI mRNA or expression vector encoding the NMI gene and a pharmaceutically acceptable carrier.

* * * * *